United States Patent
Orloff et al.

(10) Patent No.: US 10,261,032 B2
(45) Date of Patent: Apr. 16, 2019

(54) NONCONTACT RESONAMETER, PROCESS FOR MAKING AND USE OF SAME

(71) Applicants: NATIONAL INSTITUTE OF STANDARDS AND TECHNOLOGY, Gaithersburg, MD (US); Nathan Daniel Orloff, Houston, TX (US); Christian John Long, College Park, MD (US)

(72) Inventors: Nathan Daniel Orloff, Boulder, CO (US); Christian John Long, Greenbelt, MD (US); Jan Obrzut, Germantown, MD (US)

(73) Assignee: NATIONAL INSTITUTE OF STANDARDS AND TECHNOLOGY, Washington, DC (US)

( * ) Notice: Subject to any disclaimer, the term of this patent is extended or adjusted under 35 U.S.C. 154(b) by 413 days.

(21) Appl. No.: 14/958,539

(22) Filed: Dec. 3, 2015

(65) Prior Publication Data

US 2016/0161424 A1     Jun. 9, 2016

Related U.S. Application Data

(60) Provisional application No. 62/086,748, filed on Dec. 3, 2014.

(51) Int. Cl.
*G01N 22/04*     (2006.01)
*G01N 33/543*    (2006.01)
(Continued)

(52) U.S. Cl.
CPC .................... *G01N 22/00* (2013.01)

(58) Field of Classification Search
CPC ...... G01N 22/00; G01N 22/04; G01N 33/543; G01N 33/557; G01R 27/04; G01R 27/32;
(Continued)

(56) References Cited

U.S. PATENT DOCUMENTS 5,900,618 A      5/1999  Anlage et al.
7,423,435 B2 *   9/2008  Sawamoto ........... D21G 9/0009
                                                    324/644
(Continued)

OTHER PUBLICATIONS

Orloff, Nathan D., et al., "Noncontact conductivity and dielectric measurement for high throughput roll-to-roll nanomanufacturing", Scientific Reports, Nov. 23, 2015, pp. 1-8, vol. 5, No. 17019; DOI: 10.1038/srep17019.

*Primary Examiner* — Neel D Shah
(74) *Attorney, Agent, or Firm* — Office of Chief Counsel for National Institute of Standards and Technology

(57) ABSTRACT

A noncontact resonameter includes: a resonator to: produce an excitation signal including a field; subject a sample to the excitation signal; produce a first resonator signal in a presence of the sample and the excitation signal, the first resonator signal including: a first quality factor of the resonator; a first resonance frequency of the resonator; or a combination thereof, the first resonator signal occurring in an absence of contact between the sample and the resonator; and produce a second resonator signal in a presence of the excitation signal and an absence of the sample, the second resonator signal including: a second quality factor of the resonator; a second resonance frequency of the resonator; or a combination thereof; a circuit in electrical communication with the resonator to receive the first resonator signal and the second resonator signal; and a continuous feeder to: provide the sample proximate to the resonator; dispose the sample intermediately in the field of the excitation signal during production of the first resonator signal; remove the sample from the resonator; and manipulate a position of the sample relative to the resonator in a continuous motion and in an absence of contact between the sample and the resonator.

16 Claims, 26 Drawing Sheets

(51) Int. Cl.
  *G01N 33/557* (2006.01)
  *G01R 27/04* (2006.01)
  *G01R 27/32* (2006.01)
  *G01V 3/00* (2006.01)
  *G01R 33/28* (2006.01)
  *G01R 33/32* (2006.01)
  *G01R 33/46* (2006.01)
  *G01R 33/60* (2006.01)
  *G01R 33/62* (2006.01)
  *G01R 33/34* (2006.01)
  *G01N 22/00* (2006.01)

(58) Field of Classification Search
  CPC ........ G01R 33/28; G01R 33/32; G01R 33/46;
           G01R 33/60; G01R 33/62; G01R 33/341;
                    G01R 33/343; G01V 3/00
  See application file for complete search history.

(56) References Cited

U.S. PATENT DOCUMENTS

| | | | | |
|---|---|---|---|---|
| 2004/0004484 A1* | 1/2004 | Talanov | ................. | B82Y 20/00 324/633 |
| 2005/0116712 A1* | 6/2005 | Corver | ................... | G01N 24/08 324/309 |
| 2006/0192557 A1* | 8/2006 | Kloza | .................... | G01N 24/08 324/318 |
| 2010/0045306 A1* | 2/2010 | Ookubo | ................. | B82Y 35/00 324/637 |
| 2014/0218049 A1* | 8/2014 | Sawamoto | ............ | G01N 22/04 324/640 |

* cited by examiner

NONCONTACT RESONAMETER, PROCESS FOR MAKING AND USE OF SAME

CROSS REFERENCE TO RELATED APPLICATIONS

This application claims the benefit of U.S. Provisional Patent Application Ser. No. 62/086,748 filed Dec. 3, 2014, the disclosure of which is incorporated herein by reference in its entirety.

STATEMENT REGARDING FEDERALLY SPONSORED RESEARCH

This invention was made with United States Government support from the National Institute of Standards and Technology under agreement numbers 70NANB10H193 and 70NANB12H188. The Government has certain rights in the invention.

BRIEF DESCRIPTION

Disclosed is a noncontact resonameter comprising: a resonator to: produce an excitation signal comprising a field; subject a sample to the excitation signal; produce a first resonator signal in a presence of the sample and the excitation signal, the first resonator signal comprising: a first quality factor of the resonator; a first resonance frequency of the resonator; or a combination comprising at least one of the foregoing, the first resonator signal occurring in an absence of contact between the sample and the resonator; and produce a second resonator signal in a presence of the excitation signal and an absence of the sample, the second resonator signal comprising: a second quality factor of the resonator; a second resonance frequency of the resonator; or a combination comprising at least one of the foregoing; a circuit in electrical communication with the resonator to receive the first resonator signal and the second resonator signal; and a continuous feeder to: provide the sample proximate to the resonator; dispose the sample intermediately in the field of the excitation signal during production of the first resonator signal; remove the sample from the resonator; and manipulate a position of the sample relative to the resonator in a continuous motion and in an absence of contact between the sample and the resonator.

Further disclosed is a process for measuring a property of a sample, the process comprising: providing the sample to the noncontact resonameter by the continuous feeder; producing the excitation signal by the resonator; disposing the sample intermediately in the field of the excitation signal; producing the first resonator signal in a presence of the sample and the excitation signal; manipulating a position of the sample relative to the resonator in a continuous motion and in an absence of contact between the sample and the resonator; and receiving the first resonator signal by the circuit to measure the property of the sample, the property comprising an electrical property, a mechanical property, a geometric property, or a combination comprising at least one of the foregoing properties, and the property determined from the first resonator signal.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that a noncontact resonameter provides acquisition of data for a sample that is continuously fed to a resonator by a continuous feeder for determination of an electrical, mechanical, or geometric property of the sample. Further, the noncontact resonameter is configured to measure the property for the sample disposed on or part of continuous feeder that includes a web, roll, reel, wire, or capillary. A respective arrangement of the resonator and continuous feeder are selectively tailorable so that the resonator receives the sample that can have a variety of dimensions or properties. Advantageously, data for the determination of the resonance frequency and quality factor of the resonator are measured simultaneously in real time with the circuit. Without wishing to be bound by theory, it is contemplated that the resonance frequency or quality factor of the resonator relate to the property of the sample such that the property can be determined from the resonance frequency or quality factor.

Figure 1:
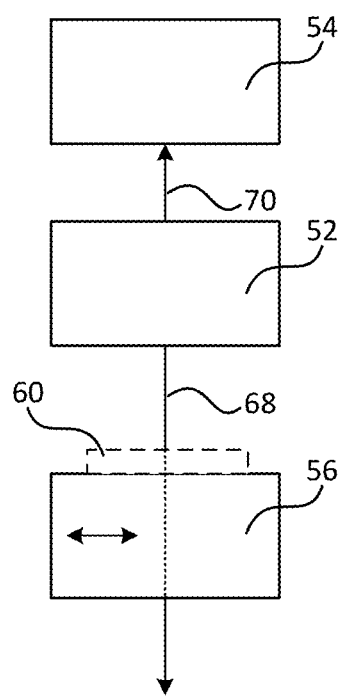
FIG. 1 shows a graph of a noncontact resonameter.

In an embodiment, with reference to FIG. 1, noncontact resonameter 50 includes continuous feeder 56 disposed proximate to resonator 52 and circuit 54 in electrical communication with resonator 52. Here, sample 60 is provided to resonator 52 via continuous feeder 56 such that resonator 52 is configured to receive continuous feeder 56 and sample 60. Further, resonator 56 produces excitation signal 68 and subjects sample 56 to excitation signal 68. In this respect, sample 56 or continuous feeder 56 are disposed intermediately in the field of excitation signal 68 as depicted by excitation field 68 extending from the resonator 52, communicating through sample 60 and continuous feeder 56, and terminating at a location beyond sample 60. Depending on a thickness of sample 60 or a property of sample 60 (e.g., dielectric constant or electrical permittivity), sample 60 may attenuate extension of excitation signal 68 beyond sample 60. As used herein, being disposed "intermediately" refers to sample 60 being disposed within the field of excitation signal 68.

Figure 2:
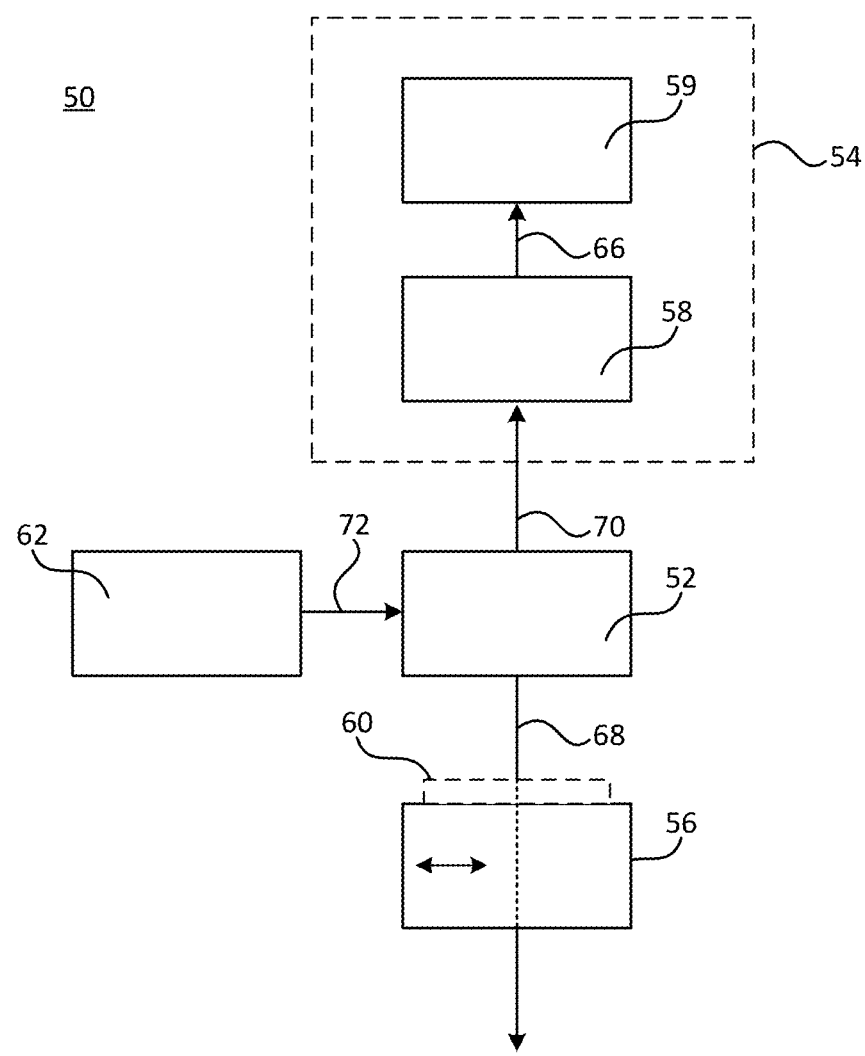
FIG. 2 shows a noncontact resonameter.

According to an embodiment, resonator 52 receives the source signal 72 (not shown in FIG. 1 but see, e.g., FIG. 2). In response to receipt of source signal 72, resonator 52 produces excitation signal 68. Moreover, resonator 52 produces excitation signal 68 in a presence or in an absence of sample 60 or continuous feeder 56. Additionally, resonator 52 produces resonator signal 70 that is communicated to circuit 54. Resonator signal 70 includes a quality factor of resonator 52, a resonance frequency of resonator 52, or combination thereof.

In some embodiments, resonator signal 70 is a first resonator signal produced by resonator 52 in a presence of sample 60 and excitation signal 68, wherein the first resonator signal includes a first quality factor of resonator 52, a first resonance frequency of resonator 52, or a combination thereof. The first resonator signal occurs in an absence of contact between sample 60 and resonator 52 with sample 60 disposed intermediately in the field of excitation signal 68.

In some embodiments, resonator 52 is operated in an absence of sample 60. Here, resonator 52 produces resonator signal 70 that is a second resonator signal in a presence of excitation signal 68 and an absence of sample 60. The second resonator signal includes a second quality factor of resonator 52, a second resonance frequency of resonator 52, or a combination thereof.

Circuit 54 is in electrical communication with resonator 52 and receives resonator signal 70 (e.g., the first resonator signal or the second resonator signal).

Continuous feeder 54 provides sample 60 proximate to resonator 52 and disposes sample 60 intermediately in the field of excitation signal 68 during production of the first resonator signal. Continuous feeder 54 also removes sample 60 from resonator 52 and manipulates (as indicated by a double-headed arrow interposed on continuous feeder 56 in FIG. 1) a position of sample 60 relative to resonator 52 in a continuous motion and in an absence of contact between sample 60 and resonator 52. It is contemplated that a distance between sample 60 and resonator 52 is controlled to position sample 60 intermediately in the field of excitation signal 68. Control of positioning of sample 60 relative to resonator 52 is accomplished by a position of continuous feeder 56 relative to resonator 52.

In an embodiment, as shown in FIG. 2, noncontact resonameter 50 includes continuous feeder 56 to provide sample 60 proximate to resonator 52 and intermediately disposed in excitation signal 68 produced by resonator 52. Source 62 provides source signal 72 (e.g., a modulated waveform) to resonator 52 that produces excitation signal 68 in response to receipt of source signal 72 from source 62. Additionally, in response to production of excitation signal 68, resonator 52 produces resonator signal 70 that is communicated to circuit 54 that includes primary detector 58 (e.g., a diode). Primary detector 58 produces detector signal 66 in response to receipt of resonator signal 70. Detector signal 66 is communicated to and received by secondary detector 59 of circuit 54.

Figure 3:
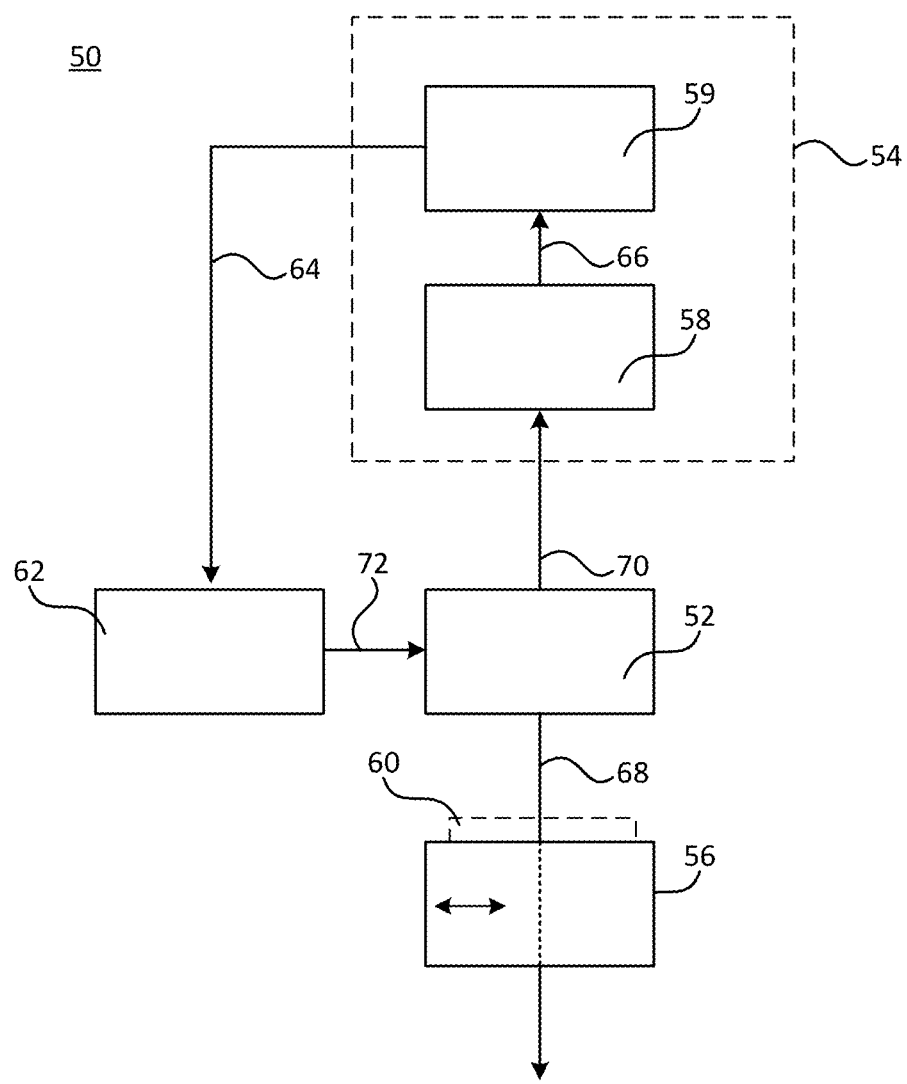
FIG. 3 shows a noncontact resonameter.

According to an embodiment, as shown in in FIG. 3, noncontact resonameter 50 includes continuous feeder 56 to provide sample 60 proximate to resonator 52 and intermediately disposed in excitation signal 68 produced by resonator 52. Source 62 provides source signal 72 (e.g., a modulated waveform) to resonator 52 that produces excitation signal 68 in response to receipt of source signal 72 from source 62. Additionally, in response to production of excitation signal 68, resonator 52 produces resonator signal 70 that is communicated to circuit 54 that includes primary detector 58 (e.g., a diode). Primary detector 58 produces detector signal 66 in response to receipt of resonator signal 70. Detector signal 66 is communicated to and received by secondary detector 59 of circuit 54, wherein secondary detector 59 produces control signal 64 is communicated to and received by source 62. It is contemplated that source signal 72 produced by source 62 includes a phase and amplitude, based on control signal 64. Accordingly, noncontact resonameter 50 shown in FIG. 3 includes circuit 54 to provide feedback to source 62 based on detection of resonator signal 70.

Figure 4:
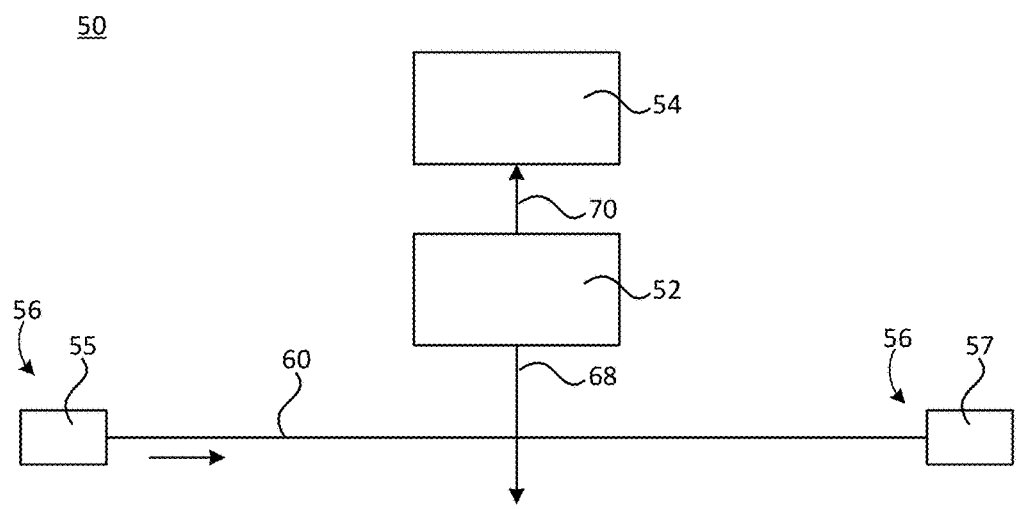
FIG. 4 shows a noncontact resonameter.

In an embodiment, as shown in FIG. 4, continuous feeder 56 includes sample source 56 to provide sample 62 resonator 52 and to intermediately disposed sample 62 in the field of excitation 68; and sample collector 57 to collect or to remove sample 62 from resonator 52. Here, sample 62 moves in a direction from sample source 55 toward sample collector 57 and traversingly passes proximate to resonator 52 as sample 52 is intermediately disposed in the field of excitation signal 68 during communication between sample source 55 and sample collector 57.

Figure 5:
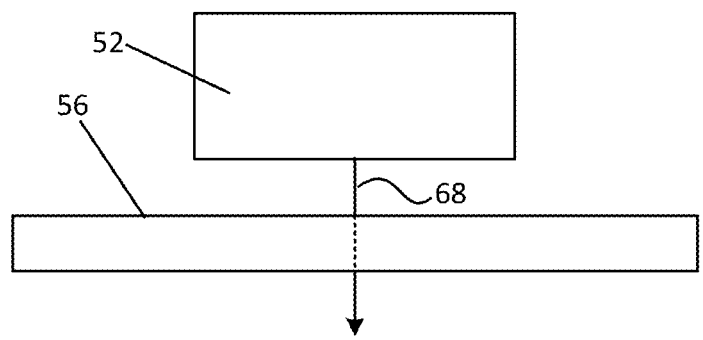
FIG. 5 shows a continuous feeder proximate to a resonator.
Figure 6:
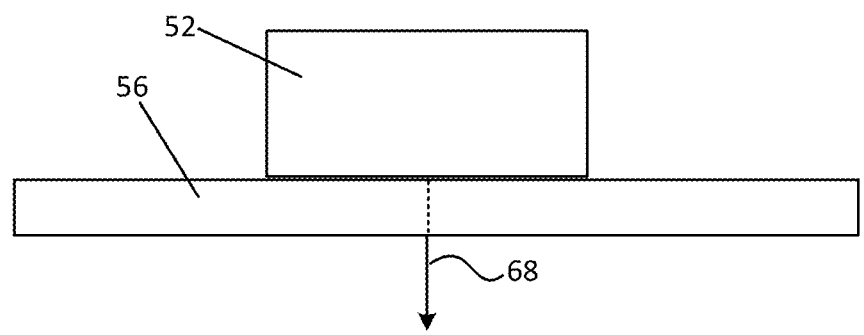
FIG. 6 shows a continuous feeder proximate to a resonator.
Figure 7:
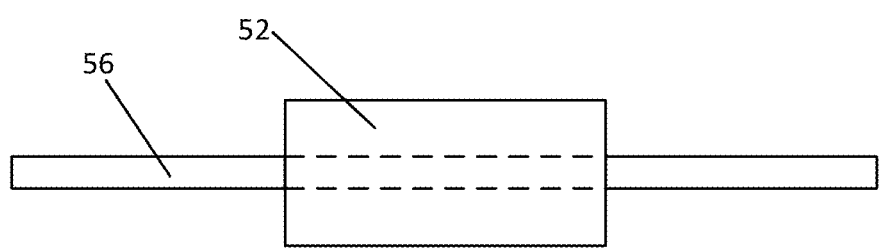
FIG. 7 shows a continuous feeder proximate to a resonator.

With reference to FIG. 5 (side view of continuous feeder 56 relative to resonator 52), FIG. 6 (side view of continuous feeder 56 relative to resonator 52), and FIG. 7 (side view of continuous feeder 56 relative to resonator 52), a distance between resonator 52 and continuous feeder 56 is selectable or adjustable. In some embodiments, an adjustment of the distance between resonator 52 and continuous feeder 56 occurs during operation of noncontact resonameter 50. In a certain embodiment, the distance between resonator 52 and continuous feeder 56 is static during operation noncontact resonameter 50. According to an embodiment, as shown in FIG. 7, continuous feeder 56 is disposed in resonator 52. It should be appreciated that the first resonator signal is produced in absence of contact between resonator 52 and sample 60 or between resonator 52 and continuous feeder 56. Accordingly, sample 60 is disposed in resonator 52 with a gap (e.g., gap 82 shown in FIG. 13, FIG. 14, and FIG. 15) between sample 60 and resonator 52 such that sample 60 is intermediately disposed in the field of excitation signal 68 when first resonator signal is produced.

Figure 8:
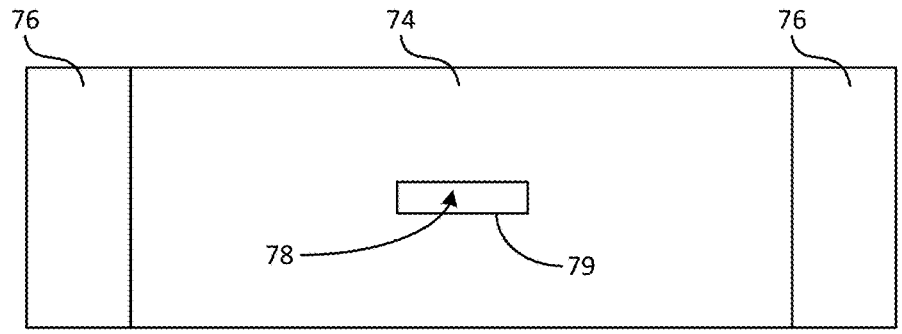
FIG. 8 shows a side view of resonator.
Figure 9:
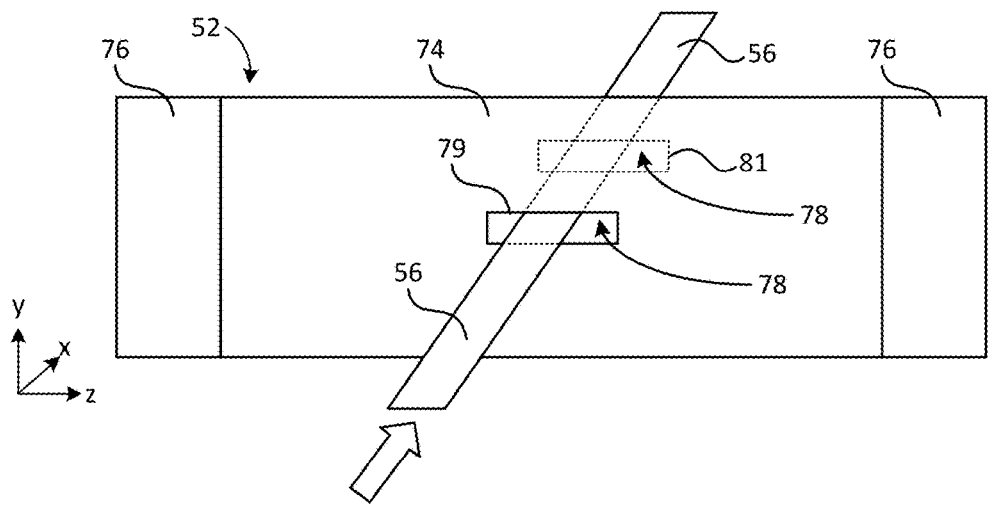
FIG. 9 shows a perspective view of a continuous feeder disposed in the resonator shown in FIG. 8.
Figure 10:
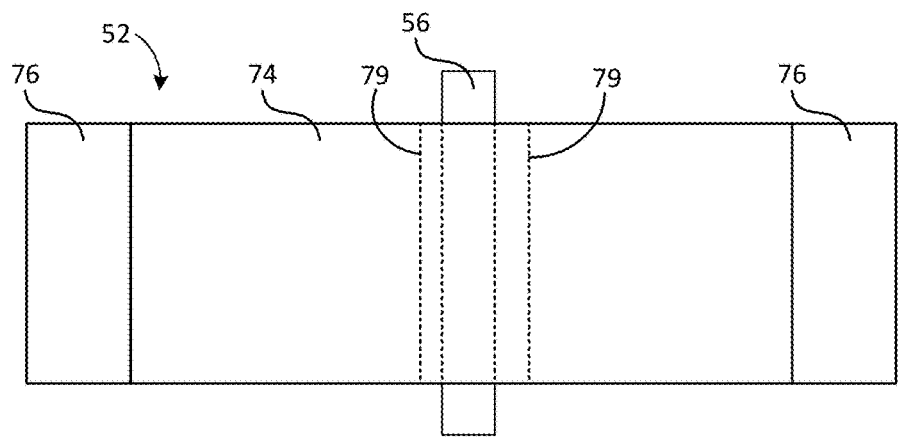
FIG. 10 shows a top view of the continuous feeder disposed in the resonator shown in FIG. 9.

In an embodiment, as shown in FIG. 8 (side view of resonator 52), resonator 52 includes waveguide 74 interposed between couplers 76; and opening 78 bounded by wall 79. As shown in FIG. 9, continuous feeder 56 is communicated through opening 78 and received by resonator 52, wherein continuous feeder 56 moves in a continuous motion through resonator 72 and exits resonator 72 through opening 81. FIG. 10 shows a top view of resonator 52 with continuous feeder 56 traversing in interior of resonator 52. Here, continuous feeder 56 can provide continuously a first portion of sample 60 to resonator 52 and removes continuously a second portion of sample 60 from resonator 52. It is contemplated that the continuous motion of continuous feeder 56 is interruptible, wherein the continuous motion of continuous feeder 56 is stopped intermittently with subsequent continuation of motion of sample 60 with respect to resonator 52 so that sample 60 completely traverse resonator 52 substantially in a single dimension of travel (e.g., in a direction provided along an x-axis shown in FIG. 9) of sample 60 relative to resonator 52, from provision of sample 60 to resonator 52 to removal of sample 60 from resonator 52. Opening (78, 81) can be disposed at a selected location on resonator 52.

Figure 11:
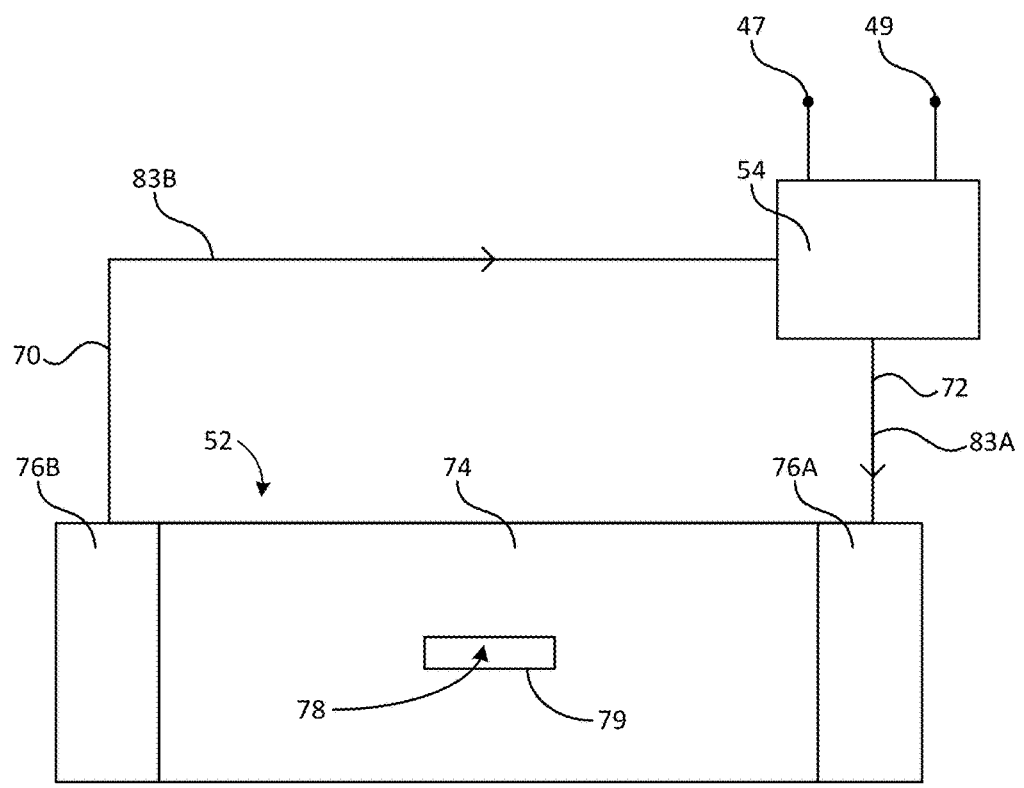
FIG. 11 shows a circuit in electrical communication with a resonator.

According to an embodiment, as shown in FIG. 11, circuit 54 is in electrical communication with resonator 52 that includes waveguide 74 and opening 78 bounded by wall 79 such that waveguide 74 is interposed between couplers (76A, 76B). Here, circuit 54 provides source signal 72 and communicates source signal 72 via signal path 83A to coupler 76A. Resonator 52 receives source signal 72 from circuit 54 via coupler 76A and produces excitation signal 68 in response to receipt of source signal 72. Waveguide 74 of resonator 52 communicates excitation signal 68 from coupler 76A to coupler 76B, and resonator signal 70 is communicated from resonator 52 via coupler 76B along signal path 83B to circuit 54. In response to receipt of resonator signal 70, circuit 54 produces first output signal 46 (not shown) and second output signal 48 that are communicated from circuit 54 respectively at first terminal 47 and second terminal 49.

Figure 12:
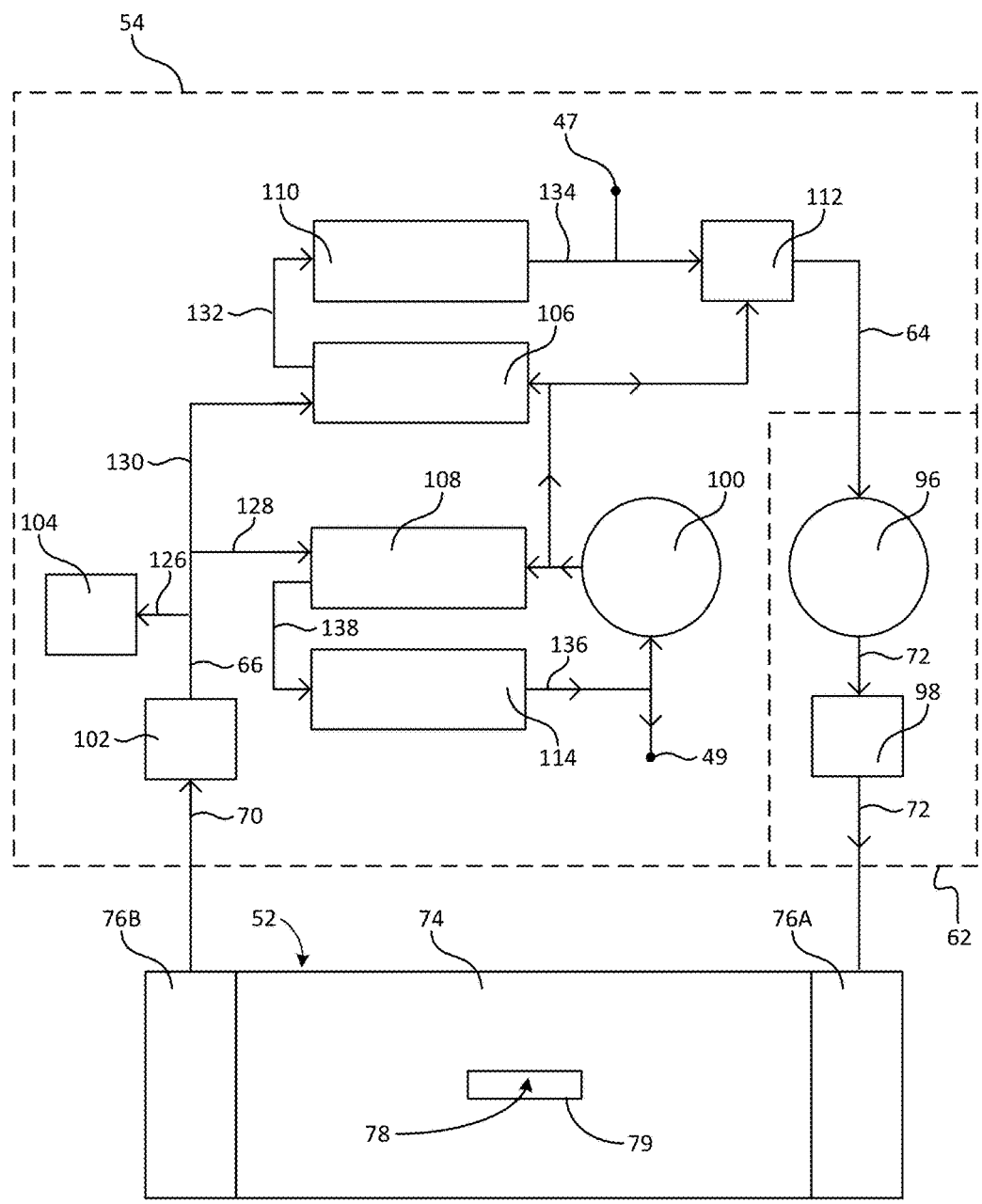
FIG. 12 shows a circuit, source, and resonator in electrical communication.

With reference to FIG. 12, in an embodiment, noncontact resonameter 50 includes resonator 52 in electrical communication with circuit 54 and source 62. Circuit 54 provides feedback to source 62 to detect a change in resonance frequency or quality factor of resonator 52. Detecting the change in resonance frequency or quality factor can occur, e.g., in real time or simultaneously. The change in resonance frequency or quality factor in resonator 52 was measured as first output signal 46 (e.g., a first voltage) and second output signal 48 (e.g., a second voltage), respectively.

Resonator 52 is excited by a frequency-modulated source signal 72 produced by voltage-controlled oscillator 96. Frequency-modulated source signal 72 is amplified by amplifier 98. Frequency source 100 controls a modulation frequency of frequency-modulated source signal 72 produced by voltage controlled oscillator 96.

A first harmonic of output power from resonator signal 70 produced by resonator 52 is used to lock a center frequency of excitation signal 68 to a resonance frequency of resonator 52 by changing an amplitude of first output signal 46. A second harmonic of output power from the resonator signal 70 produced by resonator 52 is used to adjust a depth of the frequency modulation of frequency-modulated source signal 72 by tuning second output signal 48 so that a power difference between a maximum and minimum output power during a modulation cycle is constant. Second output signal 48 is monotonically related to a quality factor of resonator 52. Diode 102 receives resonator signal 70 (which, e.g., is frequency modulated) from coupler 76B and produces detector signal 66 in response to receipt of resonator signal 70. Detector signal 66 is communicated via signal paths (126, 128, 130) from diode 102. Diode 102 is an exemplary primary detector 58, and the other components in circuit 54 are included in an exemplary embodiment of secondary detector 59.

Tunable resistor 104 terminates first signal path 126, provides control of a signal-to-noise ratio, and tunes measurement speed. Second signal path 128 electrically connects diode 102 to phase sensitive detector 106 (e.g., a lock-in amplifier) that samples at the first harmonic of frequency source 100. Third signal path 130 electrically connects diode 102 to phase sensitive detector 108 (e.g., a lock-in amplifier) that samples at the second harmonic of frequency source 100.

In-phase signal 132 of phase sensitive detector 106 is communicated to and processed with controller 110 (e.g. a proportional-integrator-derivative controller) that produces first output signal 46. First output signal 46 is communicated via signal path 134 from controller 110 to first terminal 47 and bias tee 112 (e.g., a voltage adder). First output signal 46 tunes selectively a center frequency of voltage-controlled oscillator 96 of source 62. Magnitude signal 138 of phase sensitive detector 108 is communicated to and processed with controller 114 (e.g., a proportional-integrator-derivative controller) that produces second output signal 48. Second output signal 48 is communicated via signal path 136 to frequency source 100 and controls an amplitude of the frequency modulation of voltage-controlled oscillator 96 of source 62 by changing an amplitude of frequency source 100. First output signal 46 and second output signal can be measured, e.g., as voltages, at a plurality of time intervals with a voltage sensitive device such as a data acquisition board (not shown).

Exemplary circuits 54 include homodyne detection, heterodyne detection, superheterodyne detection, in-phase and quadrature mixer, and the like. It is contemplated that circuit 54 acquires scattering parameter based on resonator signal 70 to determine the resonance frequency or quality factor of resonator 52 in real time. Moreover, acquisition of resonator signal 70 can occur whether or not sample 60 or continuous feeder 52 is disposed in resonator 52. It is contemplated that resonator signal 70 can be calibrated in an absence of sample 60 or continuous feeder 52 disposed in resonator 52. In a certain embodiment, resonator signal 70 is calibrated in a presence of a sample 60 or continuous feeder 52 having a known value of an electrical property, a mechanical property, a geometric property, or combination thereof. That is, circuit 54 include diode 102 in electrical communication with resonator 52 to receive, from resonator 52, the first resonator signal and the second resonator signal, wherein diode 102 produces detector signal 66 in response to receipt of the first resonator signal or the second resonator signal.

Source 62 includes a voltage-controlled oscillator 96 to produce source signal 72. The frequency of the source signal 72 is effective to excite resonator 52 such that resonator 52 produces excitation signal 68. In this manner, a standing wave can form, e.g., in a waveguide 74 or in free-space for a free space cavity of resonator 52 from excitation signal 68 generated by resonator 52 in response to provision of source signal 72 (having an amplitude and phase based on control signal 64). As such, source signal 72 can have a frequency, phase, amplitude, or combination thereof selected to excite resonator 52 to produce an excitation signal 68 can have electromagnetic field, acoustic field, or a combination thereof.

Resonator 52 includes a free space resonator or a cavity resonator. Further, resonator 52 can include an electromagnetic resonator, a mechanical resonator, or a combination thereof. Exemplary electromagnetic resonators include microwave resonators and the like. Exemplary mechanical resonators include acoustic resonators and the like. In an embodiment, resonator 52 is the cavity resonator, and the cavity resonator includes wall 79 bounding a sample space to receive sample 60; and opening 78 to transmit sample 60 to the sample space, wherein sample 60 does not contact resonator 52. In a particular embodiment, resonator 52 is the free-space resonator, and the free-space resonator includes a sample space to receive sample 60 spaced apart from resonator 52.

Figure 13:
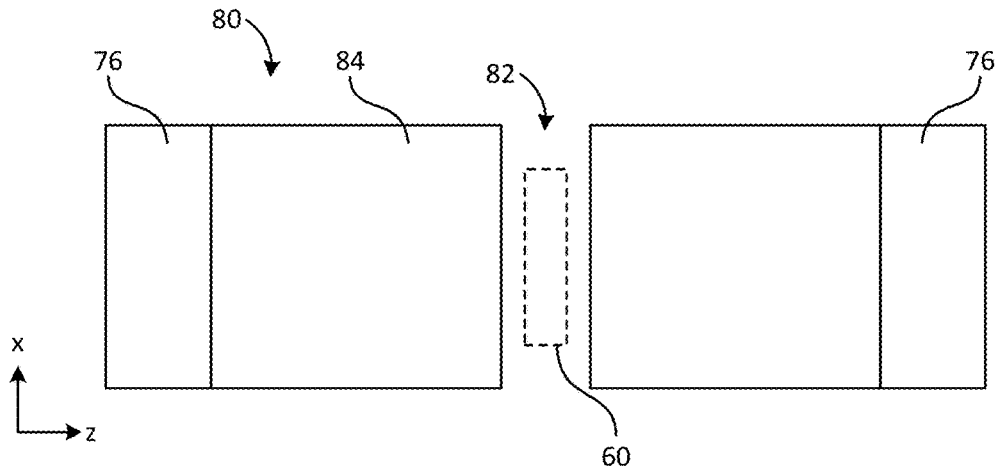
FIG. 13 shows a longitudinal cross-section of a resonator.
Figure 14:
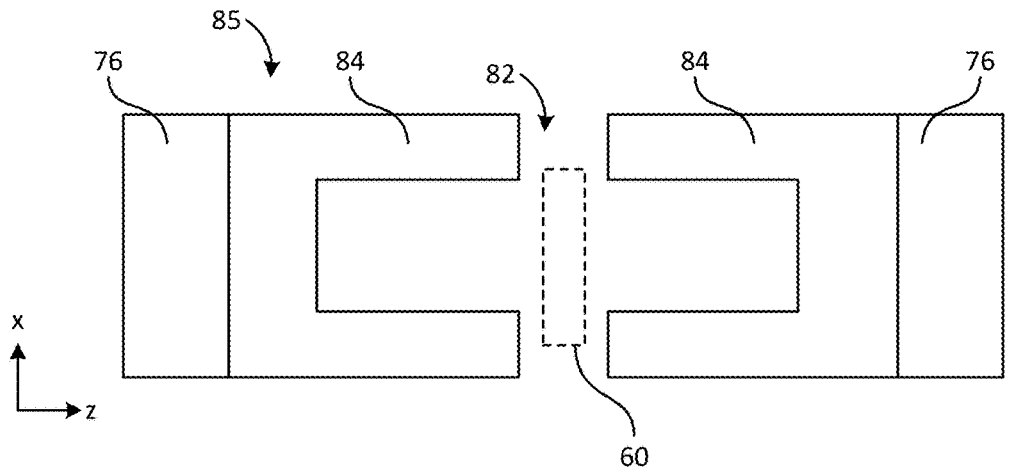
FIG. 14 shows a longitudinal cross-section of a resonator.
Figure 15:
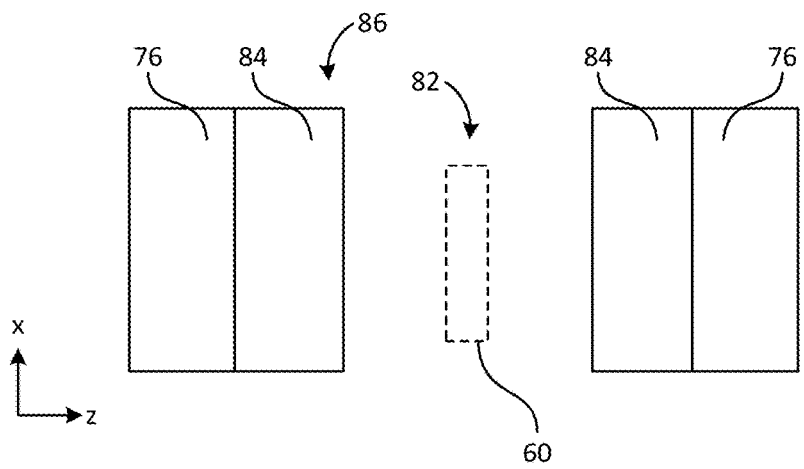
FIG. 15 shows a longitudinal cross-section of a resonator.
Figure 16:
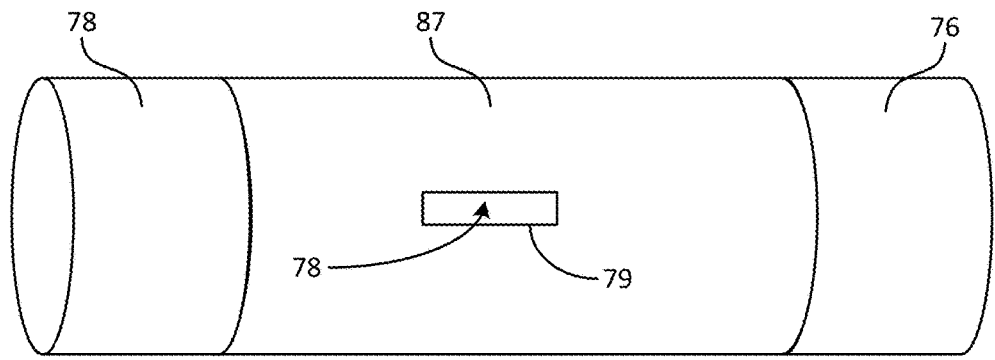
FIG. 16 shows a longitudinal cross-section of a resonator.
Figure 17:
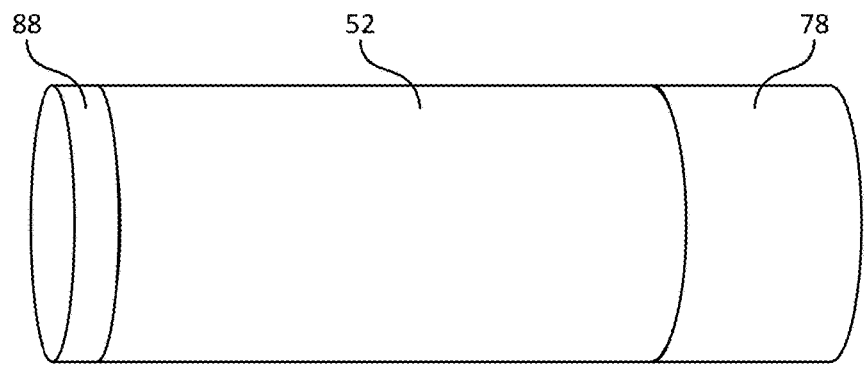
FIG. 17 shows a longitudinal cross-section of a resonator.

With reference to FIG. 13 (longitudinal cross-section of an embodiment of resonator 52), FIG. 14 (longitudinal cross-section of an embodiment of resonator 52), FIG. 15 (longitudinal cross-section of an embodiment of resonator 52), FIG. 16 (perspective view of an embodiment of resonator 52), and FIG. 17 (perspective view of an embodiment of resonator 52), exemplary resonators respectively include dielectric resonator 80 (also referred to as a split-post resonator) (FIG. 13), split-cylinder resonator 85 (FIG. 14), split capacitor resonator 86 (FIG. 15), cylindrical cavity resonator 87 (FIG. 16), and resonator with aperture 88 (FIG. 17). In an embodiment, resonator 52 includes pole 84 interposed between couplers 6 and separated by gap 82 for disposition and receipt of sample 60 or continuous feeder 56 between poles 84. Accordingly, sample 60 or continuous feeder 56 is disposed in resonator 52 and changes the resonance frequency or quality factor of resonator 52. Similarly, proximity of sample 62 aperture 88 of resonator 52 shown in FIG. 17 changes of resonance frequency or quality factor of resonator 52.

A size, shape, or type (e.g., electromagnetic or acoustic) of resonator 52 can be effective to produce excitation signal 68 in response to receipt of source signal 72. Further, the size or shape of resonator 52 can be selected to interact with sample 60 to produce resonator signal 70 that includes first resonator signal from presence of sample 60 intermediately disposed in the field of excitation signal 68. In an embodiment, resonator 52 includes a microwave resonator in which sample 60 is disposed and subjected to excitation signal 68 that includes a microwave frequency. Here, resonant signal 70 (e.g., first resonant signal) produced from interaction of excitation signal 68 with the sample 60 includes a resonant frequency or quality factor of resonator 52. In a particular embodiment, resonator 52 includes a pair of acoustic resonators opposing each other and in which sample 60 is interposed between the acoustic resonators such that excitation signal 68 is produced from receipt of source signal 72. Here, sample 60 is intermediately disposed in the acoustic field of excitation signal 68 such that resonant signal 70 (e.g., first resonant signal) produced from interaction of acoustic excitation signal 68 with sample 60 includes a resonant frequency or quality factor of resonator 52.

Continuous feeder 56 provides sample 60 to resonator 52 and dispose sample 60 intermediately in the field of excitation signal 68 during production of the first resonator signal. Additionally, continuous feeder 56 removes sample 60 from resonator 52 and manipulates a position of sample 60 relative to resonator 52 in a continuous motion and in an absence of contact between sample and resonator 52. In an embodiment, continuous feeder 56 moves sample 60 in one direction relative to resonator 52. In some embodiments, continuous feeder 56 moves sample 60 back and forth relative to resonator 52.

Figure 18:
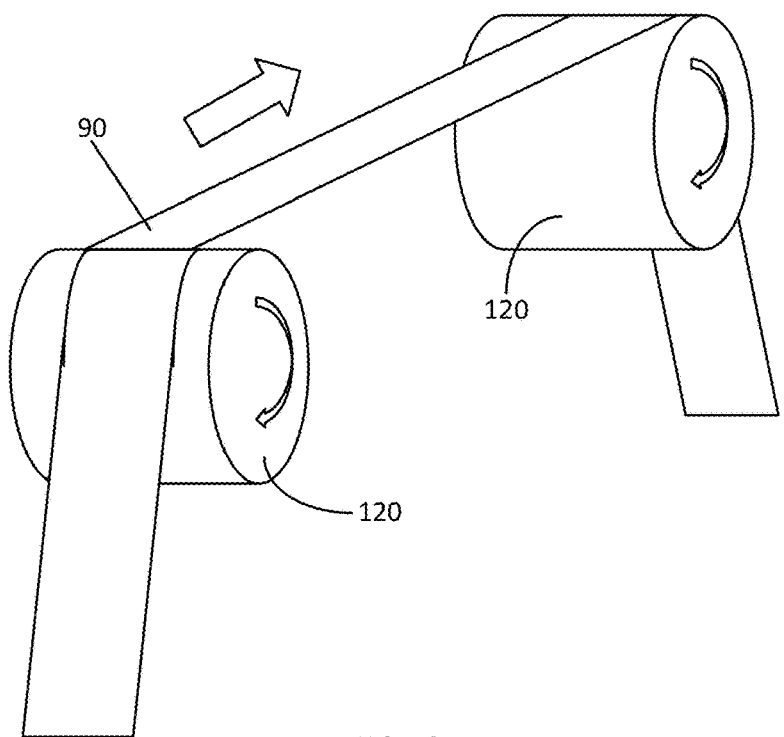
FIG. 18 shows a continuous feeder.
Figure 19:
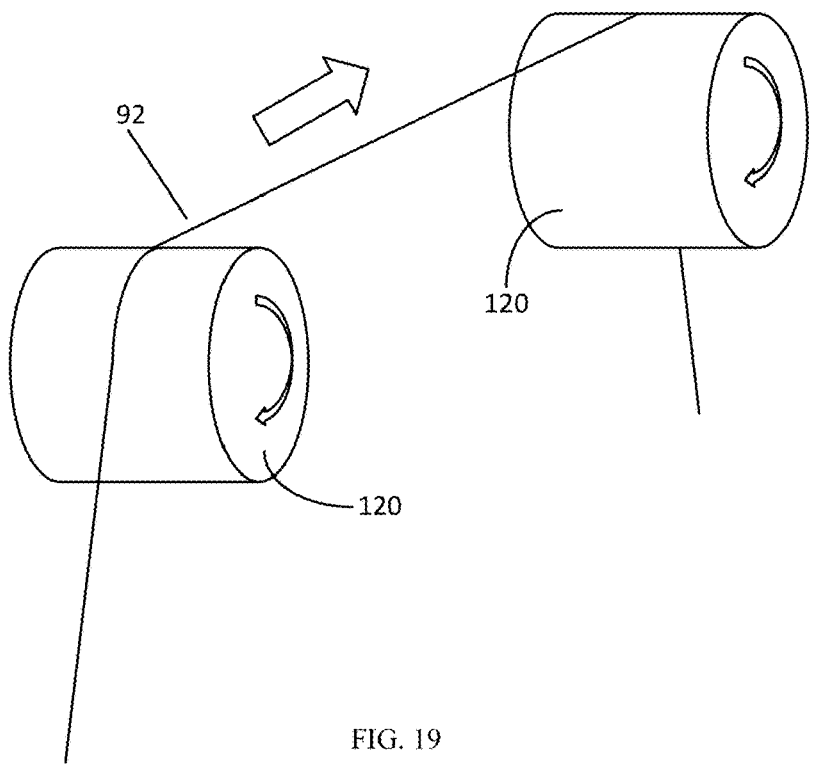
FIG. 19 shows a continuous feeder.
Figure 20:
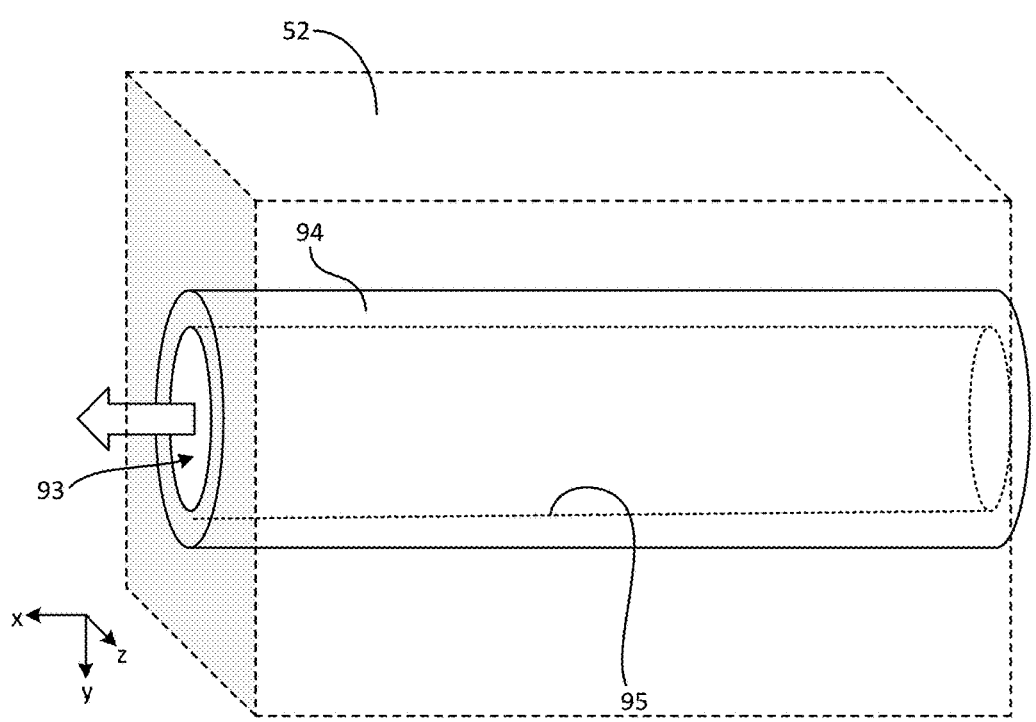
FIG. 20 shows a continuous feeder disposed in a resonator.

According to an embodiment, continuous feeder 56 includes a flexible or rigid material that translates sample 60 relative to resonator 52. Continuous feeder 56 can include rollers 120 to translate web 90, a belt, roll, and the like to position sample 60, as shown in FIG. 18. In some embodiments, continuous feeder 56 include of wire 92, a tube, cord, filament, fiber, and the like that moves sample 60 relative to resonator 52 as shown in FIG. 19. In some embodiments, as shown in FIG. 20, continuous feeder 56 includes capillary 94 disposed in resonator 52 and stationary relative to resonator 52 such that sample 60 is communicated through capillary 94 and traverses resonator 52 during passage through capillary 94. According to an embodiment, capillary 94 moves relative to resonator 52 and communicates sample 60 in an intermediate part of the field of excitation signal 68 produced by resonator 52. Here, capillary 94 includes flow path 93 bounded by wall 95. Wall 95 of capillary 94 can be isolated from resonator 52 so that capillary 94 and is not contact resonator 52. In some embodiments, capillary 94 and being contact with resonator 52 with sample 60 being subjected to excitation signal 68 in an absence of contact between sample 60 in resonator 50.

Continuous feeder provides the sample to the resonator at a feed rate effective for resonator 52 to produce resonator signal 70 from interaction of excitation signal 68. The feed rate can be from 1 micrometer per second (µm/s) to several kilometers per second (km/s), specifically from 1 mm/s to 10 km/s, more specifically from 1 cm/s to 1 km/s, and further specifically from 10 cm/s to 100 cm/s. In an embodiment, the feed rate is greater than or equal to 10 cm/s. The feed rate can be dynamic and varied from a first feed rate to a second rate, increased, decreased, or a combination thereof in a selected sequence or combination.

According to an embodiment, the continuous motion is interruptible such that continual motion of sample 60 provided by continuous feeder 56 can be stopped and then motion resumed. Moreover, continuous motion 56 occurs substantially in a single dimension of travel of sample 60 relative to resonator 52, from provision of sample 60 to resonator 52 to removal of sample 60 from resonator 52.

In an embodiment, sample 60 includes a solid, liquid, gas, or a combination thereof. Further, sample 60 can be a composition that includes a single substance or a combination of substances. Sample 60 can be composition that is homogeneous or heterogeneous. Further, sample 60 can include a gradient in a concentration of a species (e.g., an atom, molecule, complex, and the like) or a property (e.g., a gradient in dielectric constant) across a length of sample 60 provided to resonator 60. In a particular embodiment, sample 60 is a solid that includes a weave, laminate, and the like. In an embodiment, sample 60 includes the solid or liquid and a gaseous vapor of the solid or liquid. In a certain embodiment, sample 60 includes a particle disposed in a fluid, wherein sample 60 is communicated through continuous feeder and traverses resonator 52 during which time sample 60 is intermediately disposed in the field of excitation signal 68 produced by resonator 52. According to an embodiment, sample 60 is an integrated component of continuous feeder 56 provided to resonator 52, e.g., continuous feeder 56 can include web 118, wherein web 118 is a solid material that is sample 60, e.g., a polymer film. In some embodiments, sample 60 is disposed on, disposed in, transported by, or conveyed with continuous feeder 56 to be communicated to and provided to resonator 52. Here, continuous feeder 56 can include a substrate such as web 118 or capillary 94, wherein sample 60 can be a solid or liquid disposed on web 118, or a solid, liquid, or gas, that is disposed in capillary 94.

As sample 60 is communicated by continuous feeder 56 and passes intermediately through the field of excitation signal 68 produced by resonator 52, sample 60 interacts with excitation signal 68 and can change a resonant frequency or quality factor of resonator 52. Such changes are communicated as resonator signal 70 to circuit 54 from resonator 52. In this manner, noncontact resonameter 50 provides a measurement of a property of sample 60. The property includes an electrical property, a mechanical property, a geometric property (e.g., a shape, volume, thickness, dimension such a length, and the like), or a combination comprising at least one of the foregoing properties, wherein the property is determined from the first resonator signal. According to an embodiment, the property is the electrical property, and the electrical property includes a permittivity, a dielectric constant, an electrical conductivity, a permeability, or a combination thereof.

Figure 21:
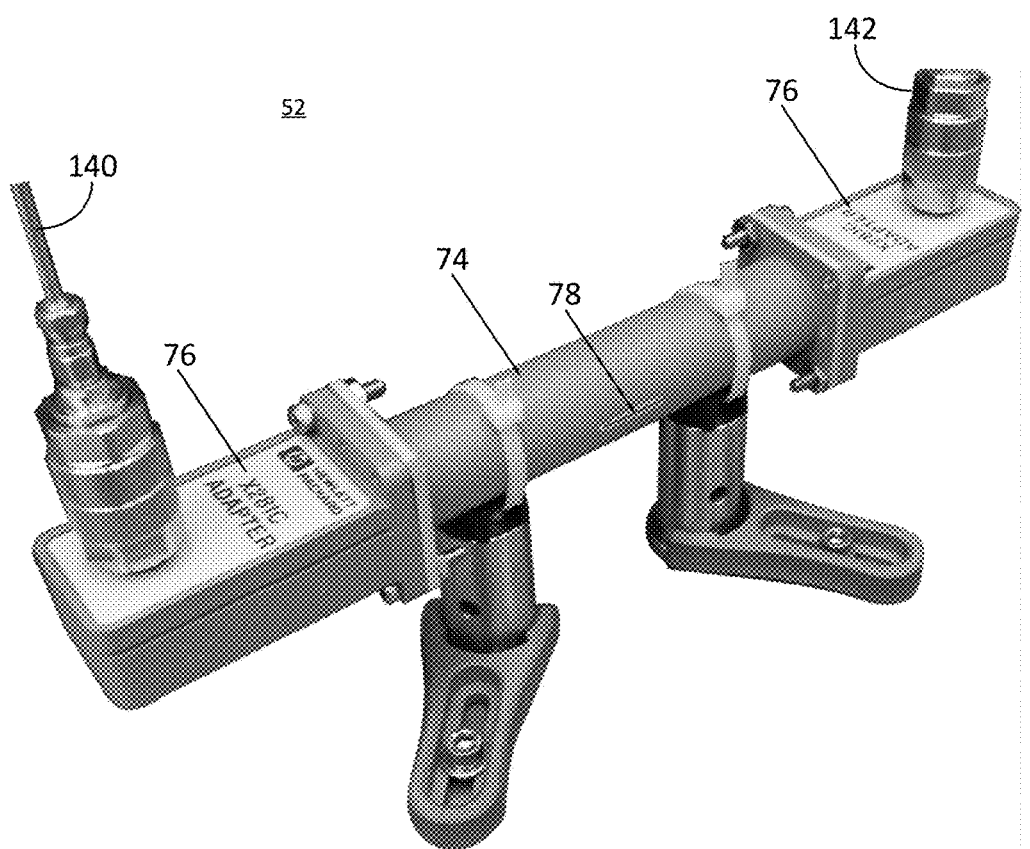
FIG. 21 shows a photograph of a resonator interposed between couplers.

In an embodiment, with reference to FIG. 21, which shows a photograph of resonator 52, resonator 52 includes waveguide 74 interposed between couplers 76. Coupler 76 includes a microwave coaxial connector to waveguide adapter. Waveguide 74 includes a rectangular waveguide, wherein coupler 76 is cross-polarized with respect to an electric field in waveguide 74. Moreover, waveguide 74 includes opening 78 for receipt of continuous feeder 56.

Figure 22:
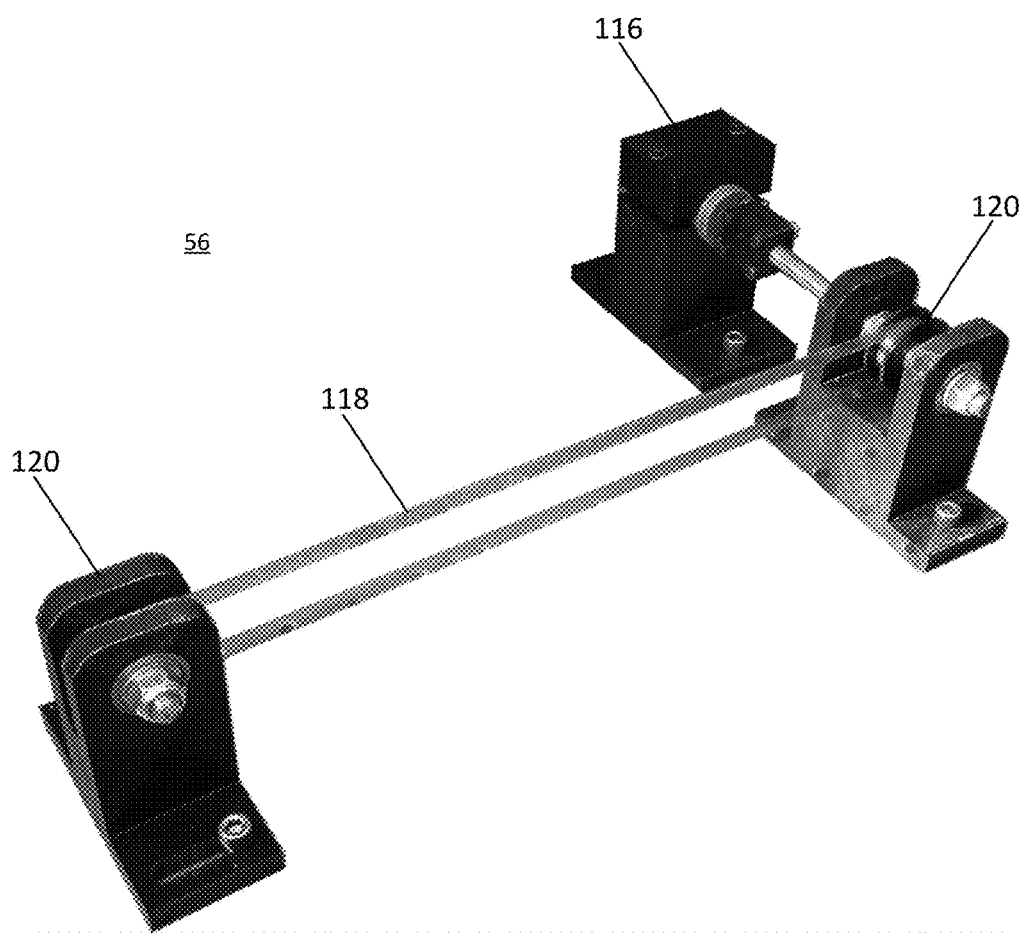
FIG. 22 shows a photograph of a continuous feeder.

Further, with reference FIG. 22, which shows a photograph of continuous feeder 56, continuous feeder 56 includes rollers 120 mounted on holders, wherein web 118 is looped around rollers 120. Motor 116 rotates rollers 120 to provide motion to continuous feeder 56 in a selectively controlled manner. Web 118 is disposed in resonator 52. When motor 116 turns rollers 120, web 118 is continuously fed through resonator 52. Additionally, sample 60 can be a discrete sample or continuous sample and disposed on web 118 to be communicated through resonator 52. In an embodiment, sample 60 is part of continuous feeder 56 (e.g., web 118). In an embodiment, sample 60 is disposed on continuous feeder 56.

Figure 23:
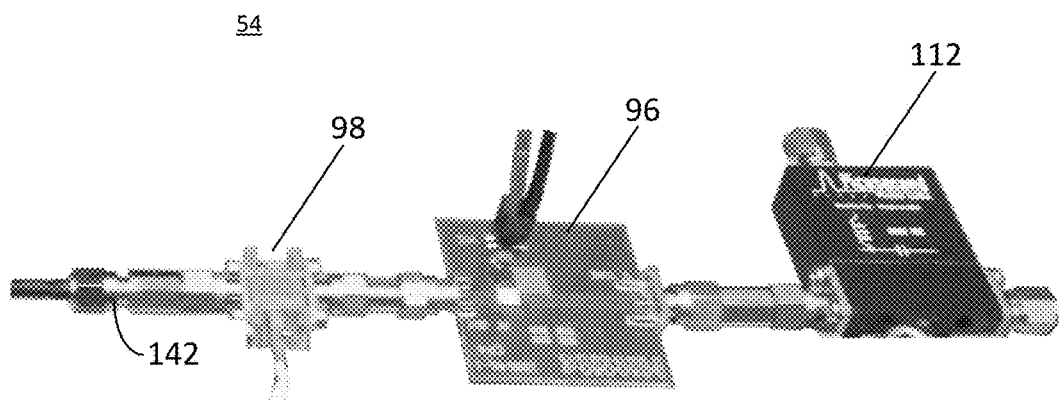
FIG. 23 shows a photograph of a circuit.

Circuit 54 receives resonant signal 70 from resonator 52 and produces control signal 64 that is communicated to source 62. FIG. 23 shows a photograph of a portion of circuit 54 and source 62 that includes bias tee 112, voltage controlled oscillator 100, and amplifier 98.

Figure 24:
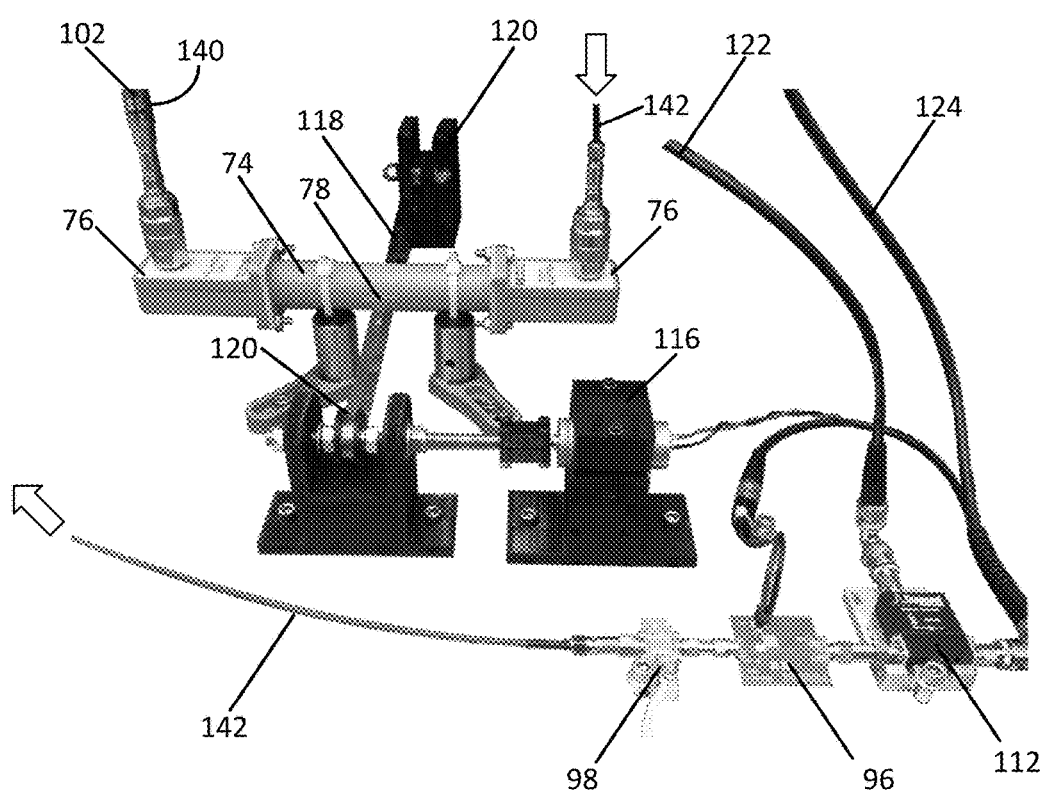
FIG. 24 shows a photograph of an arrangement of the continuous feeder shown in FIG. 22 disposed in the resonator shown in FIG. 21 that was in electrical communication with the circuit shown in FIG. 23.

With reference FIG. 24, which shows a photograph of noncontact resonameter 50 (with some electrical connections shown), noncontact resonameter 50 includes resonator 52, continuous feeder 56, and circuit 54. Here, resonator 52 is as shown in FIG. 21. Web 118 was routed through opening 78 of resonator 52 to provide a closed loop of web 118 around rollers 120 of continuous feeder 56. Motor 116 rotates rollers 120 and moves web 118. Circuit 54 (also shown in FIG. 23) connects to resonator 52 with voltage controlled oscillator 96 connected to amplifier 98 to produce source signal 72 that is communicated to resonator 52 to excite a cavity of resonator by production of excitation signal 68. Diode 102 rectifies frequency-modulated resonator signal 70 produced by resonator 52. A plurality of phase sensitive detectors (e.g., lock-in amplifiers) and integrated proportional-integrator-derivative controllers process detector signal 66 from diode 102 to produce first output signal 46 (e.g., a voltage) and second output signal 48 (e.g., a voltage). First output signal 46 is communicated to low frequency input of bias tee 112 via coaxial cable 122, and second output signal 48 is communicated to high frequency input of bias tee 112 via coaxial cable 124.

According to an embodiment, noncontact resonameter 50 includes resonator 52 to receive sample 60 and continuous feeder 56; continuous feeder 56 to provide sample 60 to resonator 52; and circuit 54 to measure the resonance frequency or quality factor of resonator 52. Resonator 52 can be detachably disposed on continuous feeder 56; continuous feeder 56 can be detachably disposed on a housing of circuit 56; or a combination thereof.

Noncontact resonameter 50 has beneficial and advantageous uses. In an embodiment, a process for measuring a property of sample 60 includes providing sample 60 to noncontact resonameter 52 by continuous feeder 56; producing excitation signal 68 by resonator 52; disposing sample 60 intermediately in the field of excitation signal 68; producing the first resonator signal in a presence of sample 60 and excitation signal 68; manipulating a position of sample 60 relative to resonator 52 in a continuous motion and in an absence of contact between sample 60 and resonator 52; and receiving the first resonator signal by circuit 54 to measure the property of sample 60. The property includes the electrical property, mechanical property, geometric property, or a combination thereof, wherein the property is determined from the first resonator signal. The property can be determined from the first resonator signal in a number of ways such as those described in the Examples provided herein.

In an embodiment, the process further includes producing the second resonator signal in a presence of excitation signal 68 and an absence of sample 60. According to an embodiment, the process includes providing source signal 72 to resonator 52 to control producing excitation signal 68 by resonator 52; and producing control signal 64 by circuit 54 to control a phase and amplitude of source signal 72.

According to an embodiment, excitation signal 68 includes an electromagnetic resonance created by resonator 52, e.g., a microwave resonance, and resonator 52 independently includes a quality factor with respect to energy storage of the electromagnetic resonance. In an embodiment, excitation signal 68 includes an acoustic resonance created by resonator 52, and resonator 52 independently includes a quality factor with respect to energy storage of the acoustic resonance.

In an embodiment, resonator 52 includes a fastener to detachably dispose continuous feed 52 to resonator 52; opening 78 (or a feed-through) in resonator 52 to receive continuous feeder 56 and sample 60; and a gap in resonator 52 to detachably dispose continuous feeder 56. In an embodiment, continuous feeder 56 includes web 118; roller 120; a reel; a wire; or a capillary to move sample 60 such as the liquid, gas, solid, or a combination thereof. According to an embodiment, resonator 52 includes: waveguide 74 that includes opening 78 to receive continuous feeder 56; dielectric resonator 80 that includes gap 82 interposed between dielectric plates detachably mounted onto continuous feeder 56; an inductor in electrical communication with a capacitor that has an opening or feed-through to receive continuous feeder 56, wherein aperture 88 can be detachably mounted onto continuous feeder 56; or a combination thereof. In an embodiment, noncontact resonameter 50 further includes continuous feeder 56, wherein continuous feeder 56 is interposed between the fastener and resonator 52 such that sample 60 can be continuously communicated and disposed in or adjacent to resonator 52.

In an embodiment, resonator 70 includes electrical contributions from continuous feeder 56 and sample 60, wherein an electrical contribution from continuous feeder 56 is removed from an electrical contribution of sample 60 in resonator signal 70. In an embodiment, circuit 54 is configured to measure the resonance frequency or quality factor of resonator 52, wherein circuit 54 can include an in-phase and quadrature mixer, a scattering parameter measurement, voltage-controlled oscillator with a feedback circuit (the feedback circuit can include a proportional-integrator-derivative signal processor, a diode, a lock-in amplifier, a bias tee, an amplifier, filter, or a combination thereof). In an embodiment, resonator 52 is configured such that the resonance frequency or quality factor of resonator 52 is changed by presence of sample 60 or continuous feeder 56. In an embodiment, circuit 54 is configured to measure the change in the resonance frequency and quality factor of resonator 52. In an embodiment, the property of sample 60 (e.g., the dielectric constant, electrical conductivity, and the like) with a known geometry is determined from the change in the resonance frequency or quality factor due to presence of sample 60 disposed intermediately in the field of excitation signal 68 produced by resonator 52. According to an embodiment, the change in the resonance frequency and quality factor due to the presence of sample 60 is used to determine a complex permeability for sample 60 in view of a known geometry of sample 60. According to an embodiment, the change in the resonance frequency and quality factor of resonator 52 due to presence of sample 60 in the field of excitation signal 68 is used to determine a thickness or geometric property for sample 60 having a known complex permittivity or complex permeability. Moreover, a loss tangent for sample 60 can be determined.

Noncontact resonameter 50 advantageously can be used to measure properties of sample 60 that is involved in a processing or manufacturing facility that includes a web, roll-to-roll, or liquid handling, wherein a feed rate or speed of sample 60 conveyed in such environment is several kilometers per hour and continuously producing materials that are used in commercial applications such as pharmaceutical, chemical, or materials manufacturing. Here, the property of sample 60 (e.g., materials properties that correlate to electrical conductivity or dielectric constant) is determined during operation and online using noncontact resonameter 50 that provides a nondestructive, noncontact inline test for the property or quality control of conditions involving sample 60. Beneficially, noncontact resonameter 50 provides a nondestructive electromagnetic (e.g., microwave) or acoustic resonator 52 to measure the property of sample 60 such as dielectric constant or electrical conductivity, at production speeds with a responsivity to change or absolute determination of the property in real time or at a selected interval of time (e.g., on a microsecond time scale). Moreover, a portion of sample 60 or substantially all of sample 60 can be subjected to excitation signal 60 such that resonator signal 70 includes data pertinent to the portion or all of sample 60 provided intermediately to the field of excitation signal 68 produced by resonator 52. Furthermore, the property of sample 60 can be determined quantitatively or qualitatively.

Figure 25:
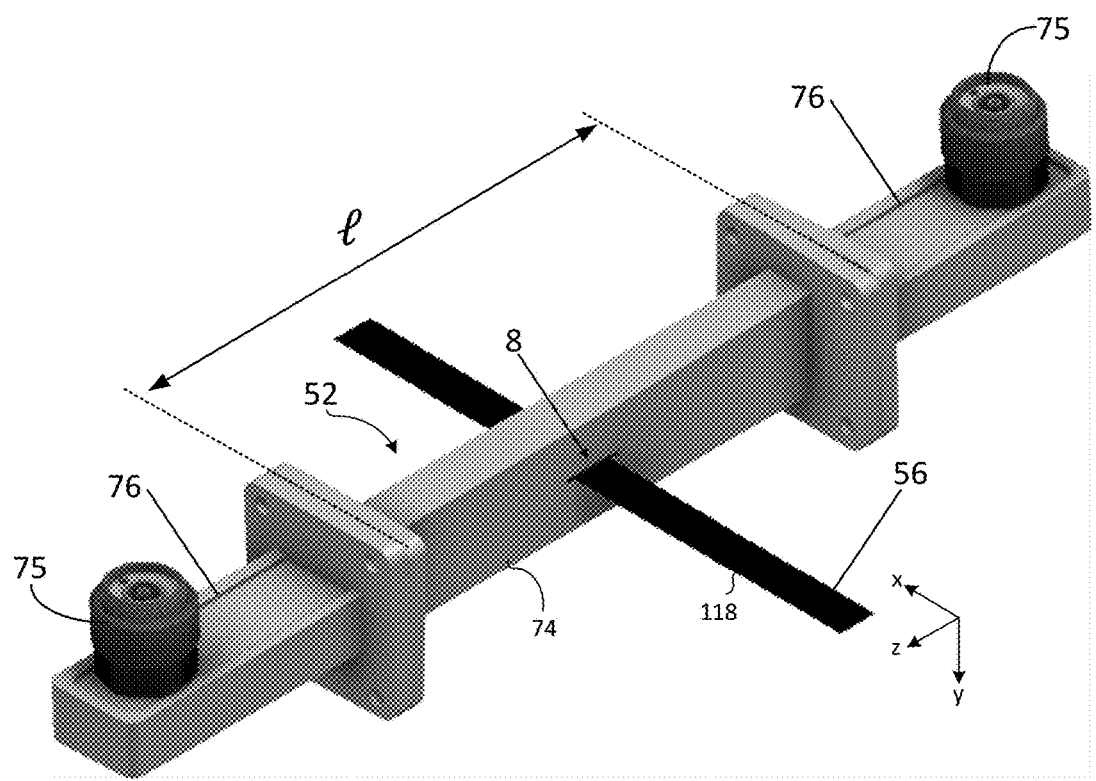
FIG. 25 shows a continuous feeder disposed in a resonator.
Figure 26:
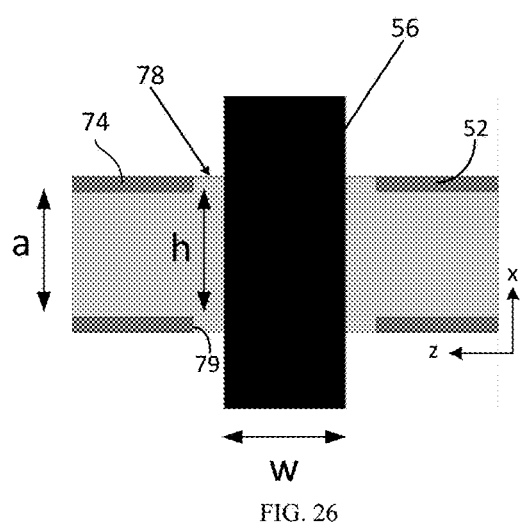
FIG. 26 shows a portion of a longitudinal cross-section in an x-z plane of the resonator shown in FIG. 25.
Figure 27:
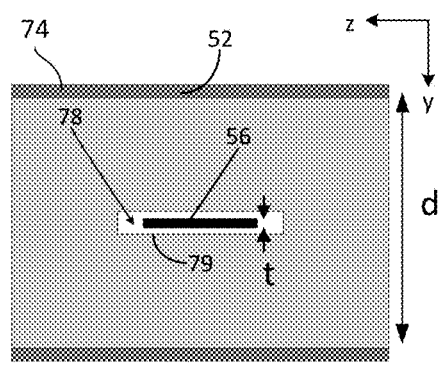
FIG. 27 shows a portion of a transverse cross-section in a y-z plane of the resonator shown in FIG. 25.

In an embodiment, noncontact resonameter 50 is used to determine the electrical property of sample 60 from the resonance frequency or quality factor from resonator signal 70 produced by resonator 52. Without wishing to be bound by theory, a process for determining the electrical property includes applying a cavity perturbation equation (e.g., discussed below) to resonator signal 70 data. Cavity perturbation equations relate resonance frequency and quality factor of resonator 52 to electrical properties of sample 60 and include properties of resonator 52 such as a sample volume or geometry of resonator 52. As shown in FIG. 25, continuous feeder 56 includes web 118 that is continuously communicated through resonator 52. Waveguide 74 of resonator 52 has dimensions that include cavity height a, cavity thickness d, and cavity width l. Web 118 of continuous feeder 52 (or sample 60) has dimensions that include sample height h, sample thickness t, and the sample width w. FIG. 26 shows a portion of a longitudinal cross-section in an x-z plane that includes continuous feeder 52 top and waveguide 74. FIG. 27 shows a transverse cross-section in a y-z plane that includes continuous feeder 52 and waveguide 74.

The cavity perturbation equations are derived from Maxwell's equations and solved for a real part of complex permittivity ($\epsilon_r$) and an imaginary part of the complex permittivity ($\epsilon_i$) of the sample. The real part of the dielectric constant is provided by formula (1).

$$\frac{\omega_c - \omega_{cs}}{\omega_c} \approx 2 \cdot \left(\frac{V_s}{V_c}\right)(\epsilon_r - 1) + b_r. \tag{1}$$

wherein in formula 1 $\omega_c$, is the resonance frequency of resonator 52; $\omega_{cs}$ is the resonance frequency of resonator 52 in a presence of sample 60 or continuous feeder 52; $V_c$ is the volume of the cavity of resonator 52; $V_s$ is the effective volume of sample 60 or continuous feeder 52 disposed in the cavity of resonator 52; and $b_r$ is an intercept. The effective sample volume $V_{cs}$ is effective because the electromagnetic field of excitation signal 68 is distributed non-uniformly over sample 60. Here, waveguide 74 is a cavity having a rectangular shape, which has an electromagnetic mode of a resonance provided by parameter n. In some embodiments, effective sample volume Vs is provided by formula (2), $$V_s = h \cdot \left(\frac{t}{2} + \frac{d}{2\pi}\sin\left(\frac{\pi t}{d}\right)\right) \cdot \left(\frac{w}{2} + \frac{\ell}{2\pi n}\sin\left(\frac{n\pi w}{\ell}\right)\right) \quad (2)$$

wherein h is sample height; t is sample thickness; w is sample width; a is cavity height; d is cavity thickness; and l is cavity width. Cavity volume $V_c$ is provided by formula (3), $$V_c = a \cdot d \cdot l. \quad (3)$$

The imaginary part of the dielectric constant is provided by formula (4), $$\frac{1}{Q_{cs}} - \frac{1}{Q_c} \approx 4 \cdot \left(\frac{V_s}{V_c}\right)\epsilon_i + b_i. \quad (4)$$

wherein $Q_c$ is the quality factor of resonator 52; $Q_{cs}$ is the quality factor of resonator 52 having sample 60 or continuous feeder 56 disposed in waveguide 74; and $b_i$ is an intercept. In some embodiments, intercepts $b_r$ and $b_i$ account for parasitic fields and can constant or finitely small (e.g., substantially having a value that is close to zero).

The articles and processes herein are illustrated further by the following Examples, which are non-limiting.

EXAMPLES

Example 1. Continuous Measurement of First Voltage (First Output Signal) and Second Voltage (Second Output Signal)

Figure 28:
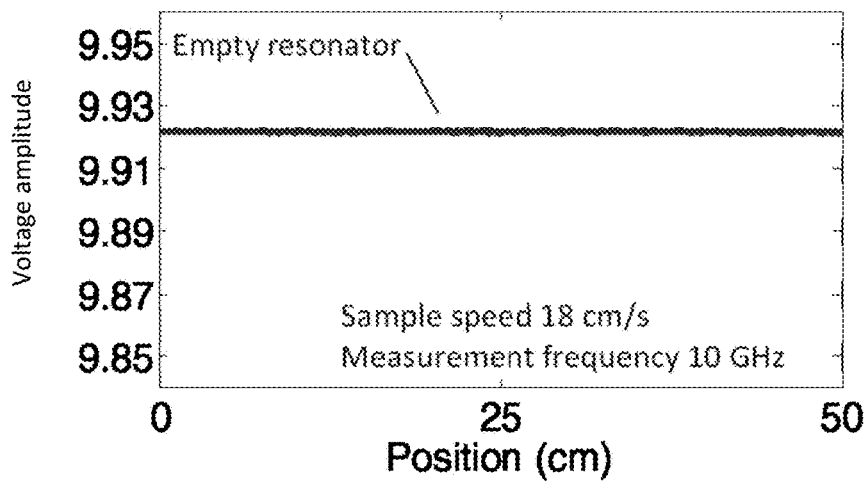
FIG. 28 shows a graph of voltage versus position for an empty resonator.
Figure 29:
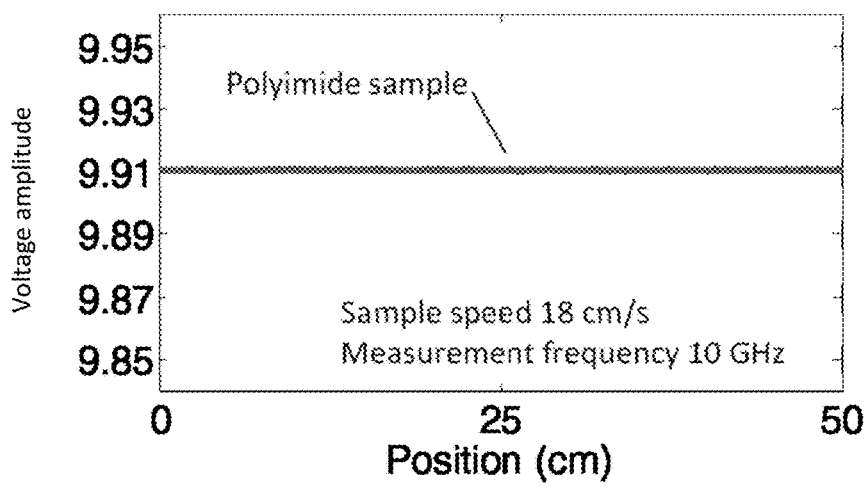
FIG. 29 shows a graph of voltage versus position for a sample disposed in a resonator.
Figure 30:
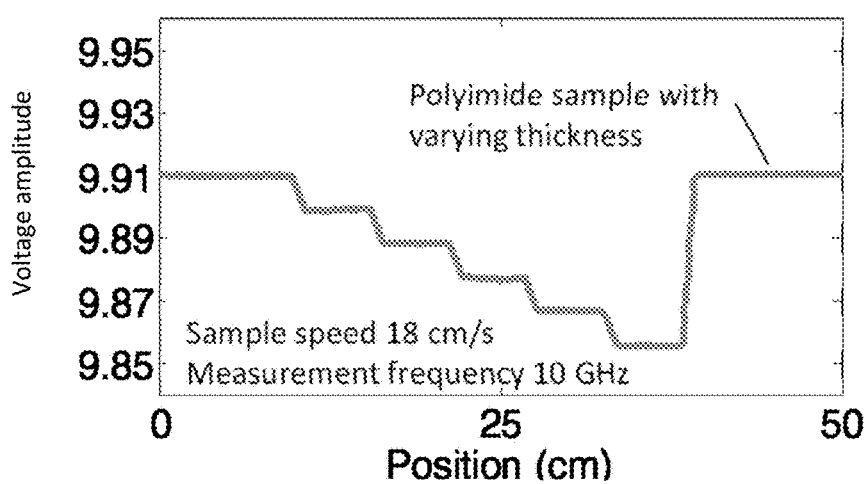
FIG. 30 shows a graph of voltage versus position for a sample disposed in a resonator.

A noncontact resonameter as shown in FIG. 24 was provided and included circuit 54 as shown in FIG. 12. The in-phase signal of lock-in amplifier 106 was processed with proportional-integrator-derivative controller 110, as shown in FIG. 12. Proportional-integrator-derivative controller 110 produced first output signal 46 that was recorded as sample 60 was continuously fed through resonator 52. Three measurements were made with noncontact resonameter 50 for first output signal 46. In a first measurement, first output signal 46 was measured without sample 60 disposed in resonator 52. In a second measurement, sample 60 included web 118 that was fabricated to include a polyimide strip that was 70 cm long. An amplitude of first output signal 46 (measured as a voltage) was shifted by approximately a constant relative to the amplitude of first output signal 46 from resonator 52 without sample 60. The polyimide web 118 was communicated through resonator 52 at a feed rate of 18 cm/s for a length of 50 cm of sample 60. A staircase pattern of sample 60 was made wherein the polyimide was formed in steps having 6 cm lengths with an equivalent thickness increase per step. As a result of varying thickness of polyimide sample 60, the amplitude of first output signal 46 shifted by an increasing amount relative to the amplitude of first output signal 46 measured from resonator signal of resonator 52 without sample 60 disposed therein. FIG. 28, FIG. 29, and FIG. 30 show graphs of voltage amplitude of first output signal 46 versus position along sample 60 respectively for empty resonator 52 (absence of sample 60 in resonator 52), monotonic thickness sample 60, and sample 60 that had a staircase pattern with incremental thickness.

Figure 31:
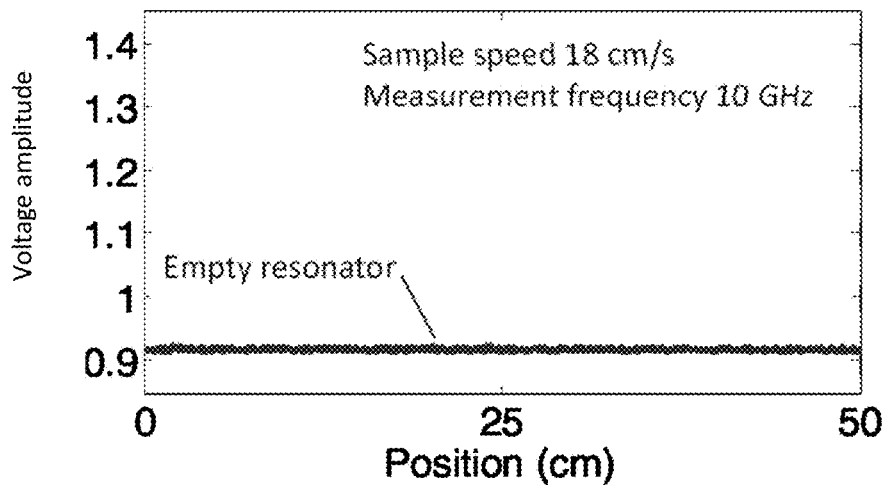
FIG. 31 shows a graph of voltage versus position for an empty resonator.
Figure 32:
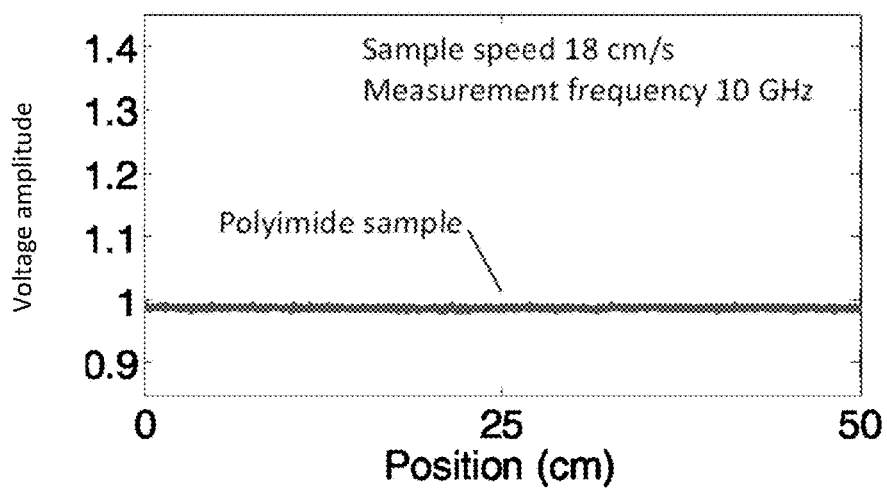
FIG. 32 shows a graph of voltage versus position for a sample disposed in a resonator.
Figure 33:
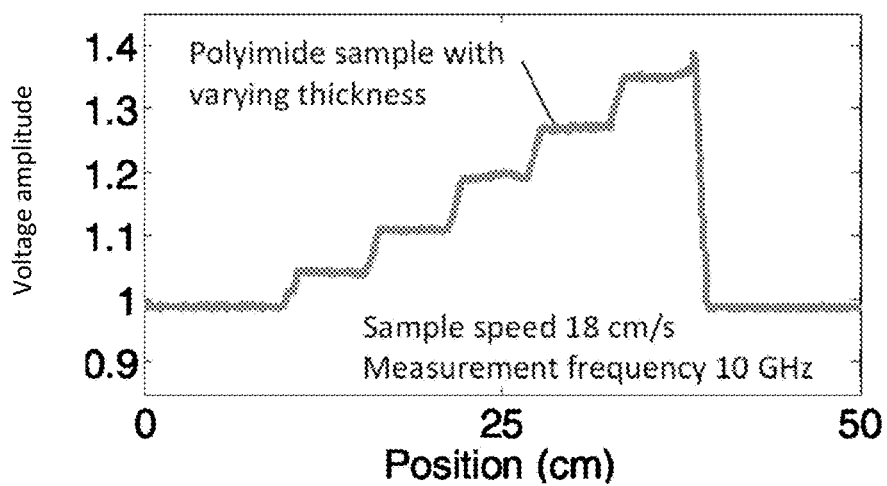
FIG. 33 shows a graph of voltage versus position for a sample disposed in a resonator.

The magnitude signal of lock-in amplifier 108 was processed by proportional-integrator-derivative controller 114 (see FIG. 12), and controller 114 produced second output signal 48 that was obtained as sample 60 was continuously fed through resonator 52. Noncontact resonator 50 made three measurements for second output signal 48. In a first measurement, second output signal 48 was measured without sample 60 disposed in resonator 52. In a second measurement, sample 60 included web 118 that was fabricated to include a polyimide strip that was 70 cm long. An amplitude of second output signal 48 (measured as a voltage) was shifted by approximately a constant relative to the amplitude of second output signal 48 from resonator 52 without sample 60. The polyimide web 118 was communicated through resonator 52 at a feed rate of 18 cm/s for a length of 50 cm of sample 60. A staircase pattern of sample 60 was made wherein the polyimide was formed in steps having 6 cm lengths with an equivalent thickness increase per step. As a result of varying thickness of polyimide sample 60, the amplitude of second output signal 48 shifted by an increasing amount relative to the amplitude of second output signal 48 measured from resonator signal 70 of resonator 52 without sample 60 disposed therein. FIG. 31, FIG. 32, and FIG. 33 show a graph of voltage amplitude of second output signal 48 versus position along sample 60 respectively for empty resonator 52 (absence of sample 60 in resonator 52), monotonic thickness sample 60, and sample 60 that had a staircase pattern with incremental thickness.

The amplitude of first output signal 46 related to the resonance frequency of resonator 52, and the amplitude of the second output signal 48 related to the quality factor of resonator 52. Where first output signal 46 and second output signal 48 are voltages, first output signal 46 and second output signal 48 can be used directly without and further analysis of data to determine, e.g., a relative change in resonant frequency or change in quality factor.

Example 2. Calibration of Circuit to Obtain Resonant Frequency and Quality Factor of Resonator Circuit 54 was used to calibrate the resonance frequency and quality factor of resonator 52 of the noncontact resonator of Example 1. The calibration quantitatively related first output signal 46 (e.g., an amplitude of its voltage) and second output signal 48 (e.g., an amplitude of its voltage) measured by circuit 54 to the resonance frequency and quality factor of resonator 52. The calibration was performed in two sets of measurements. In the first measurement, sample 60 was disposed in resonator 52 in a plurality of discrete steps in which the amount of sample 60 disposed in an interior of resonator 52 increased from 0% to 100%. At each insertion, a vector network analyzer measured scattering parameters of resonator 52 as a function of frequency.

Figure 34:
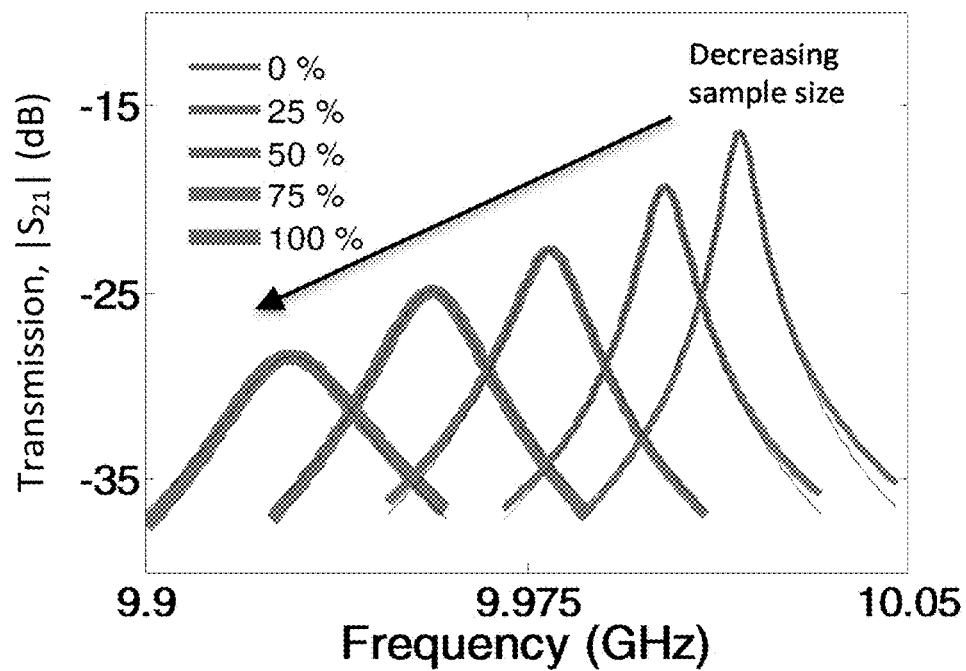
FIG. 34 shows a graph of transmission versus frequency.
Figure 35:
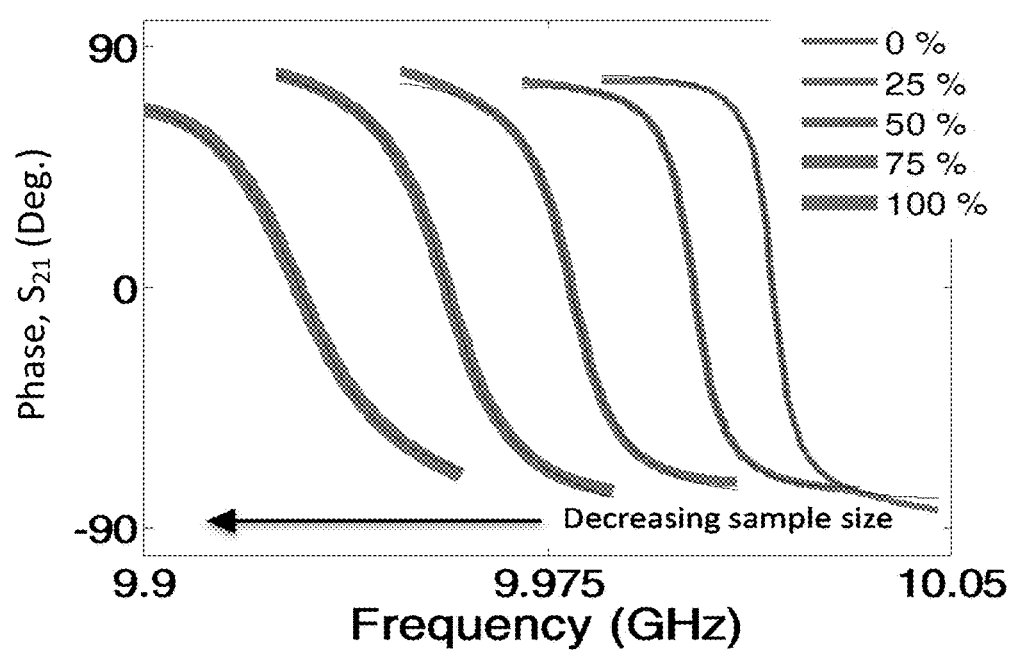
FIG. 35 shows a graph of phase versus frequency.

The scattering parameters were fit to a damped harmonic oscillator model as a function of frequency. FIG. 34 shows a graph of magnitude of the transmission $|S_{21}|$ versus frequency, and FIG. 35 shows a graph of the phase $S_{21}$ of the transmission versus frequency. The damped harmonic oscillator equation provided an amplitude and phase such that transmission T is $T(\omega) = A(\omega)e^{i\phi(\omega)}$, wherein $A(\omega)$ is the amplitude as provided in formula (5), and $\phi(\omega)$ is the phase as provided in formula (6).

$$A(\omega) = \frac{2A_o\zeta\omega_o^2}{(\omega_o^2 - \omega^2)^2 + (2\zeta\omega_o\omega)^2} \quad (5)$$

-continued $$\phi(\omega) = -\arctan\left(\frac{2\zeta\omega_o\omega}{\omega_o^2 - \omega^2}\right) + m_o\omega + \phi_o \qquad (6)$$

Amplitude $A(\omega)$ included three fit parameters, i.e., amplitude $A_o$ of the signal, resonance frequency $\omega_o$, and damping ratio $\zeta$. Phase $\phi(\omega)$ included two fit parameters, i.e., delay $m_o$, and phase offset $\phi_o$. The scattering parameters were fit to formula (5) and formula (6) as a function of frequency. Here, $\omega_o$ was the resonance frequency of resonator 52, and the damping ratio was related to the quality factor of resonator 52 as $1/2\zeta$.

After the quality factor and resonance frequency of resonator 52 was determined as a function of insertion percentage of sample 60 in resonator 52, first output signal 46 and second output signal 48 were measured with sample 60 disposed in resonator 52 at the same selected insertion values.

Figure 36:
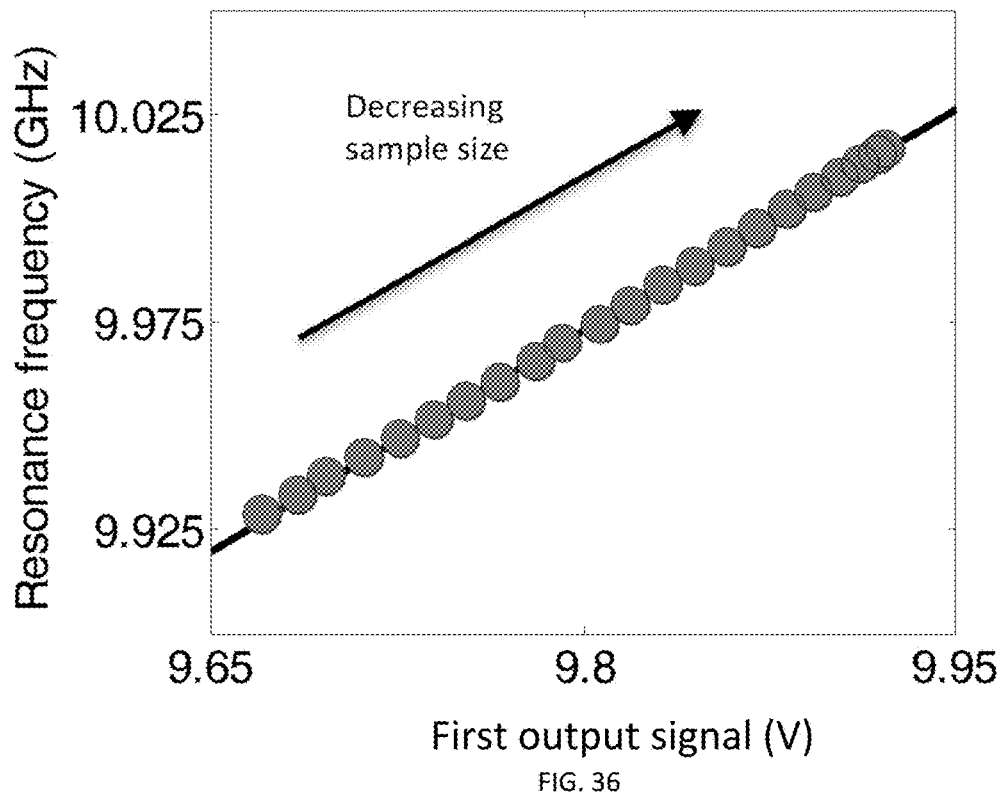
FIG. 36 shows a graph of phase versus frequency.
Figure 37:
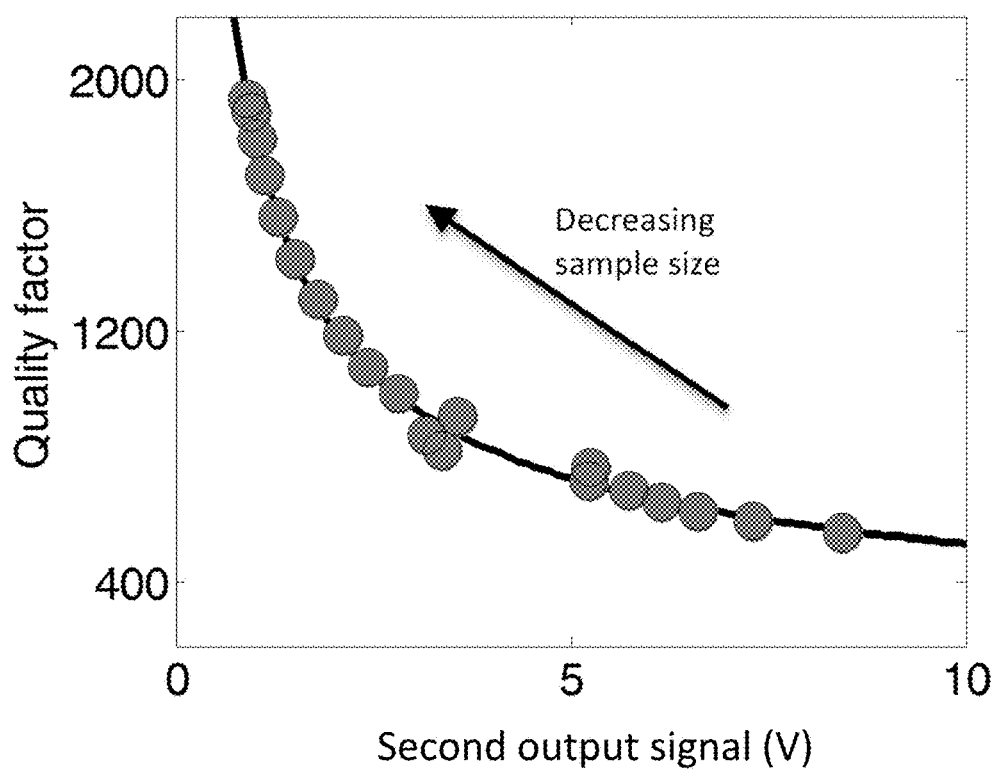
FIG. 37 shows a graph of phase versus frequency.

FIG. 36 shows a graph of resonance frequency of resonator 52 versus first output signal 46, and a best fit line to the data is also shown. FIG. 37 shows a graph of quality factor of resonator 52 versus second output signal 48, and a best fit line to the data is also shown.

Figure 38:
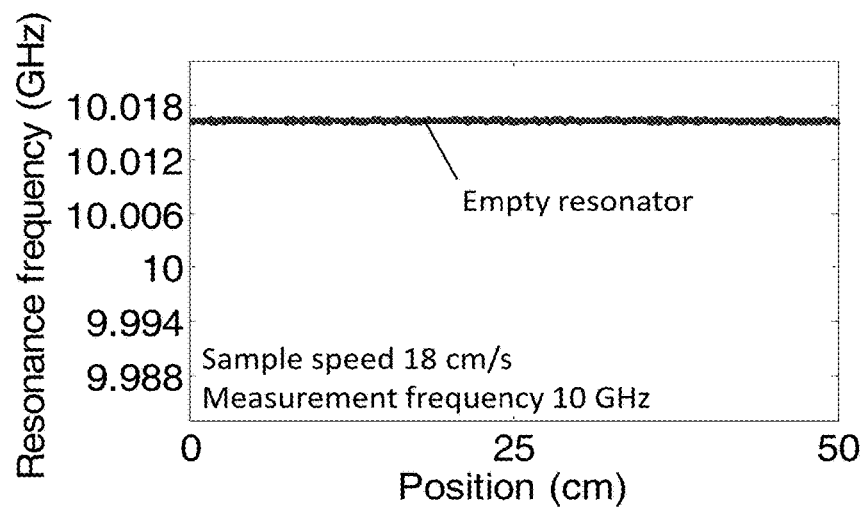
FIG. 38 shows a graph of resonance frequency versus position for an empty resonator.
Figure 39:
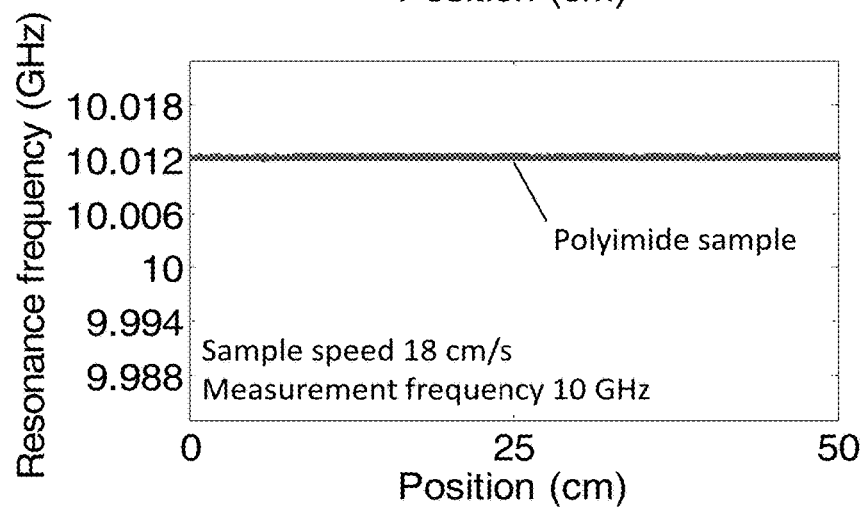
FIG. 39 shows a graph of resonance frequency versus position for a sample disposed in a resonator.
Figure 40:
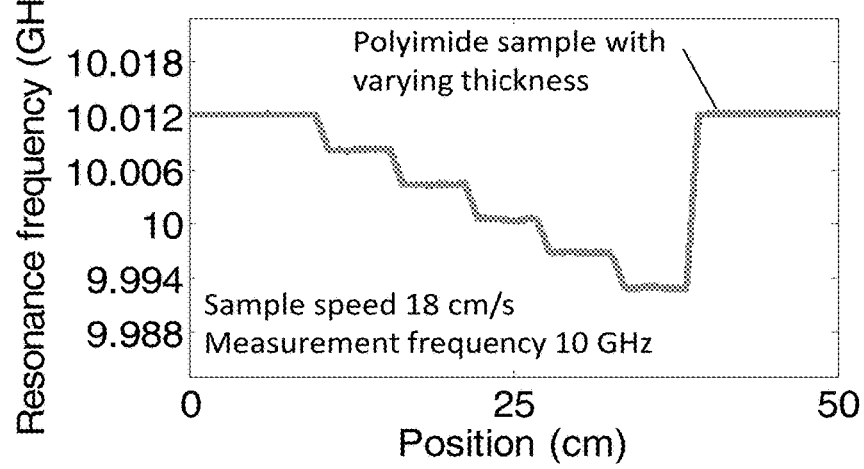
FIG. 40 shows a graph of resonance frequency versus position for a sample disposed in a resonator.
Figure 41:
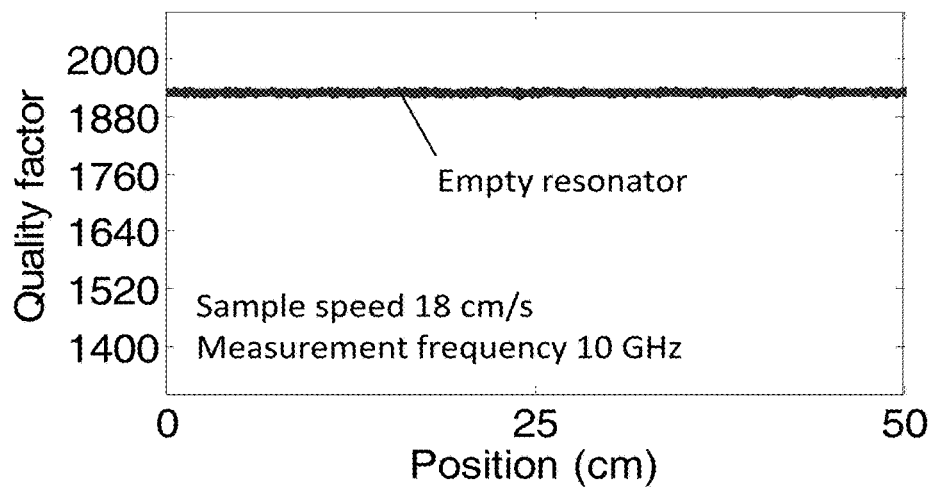
FIG. 41 shows a graph of quality factor versus position for an empty resonator.
Figure 42:
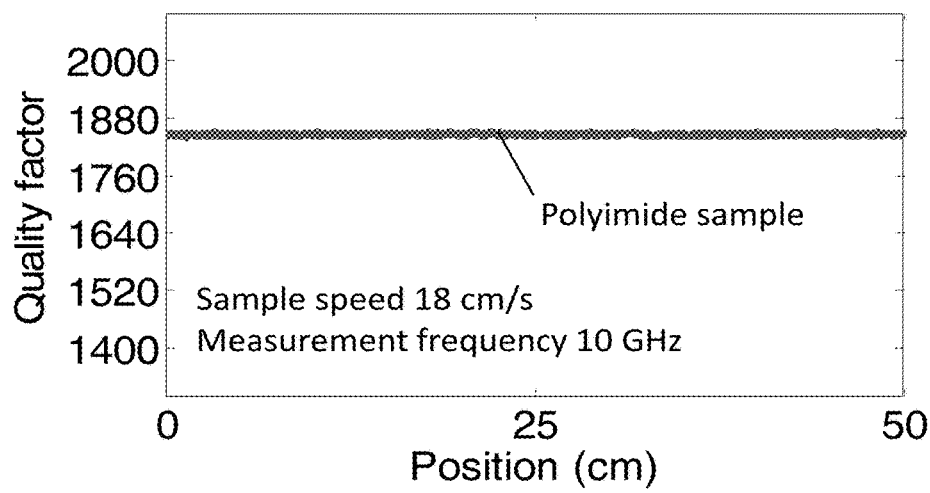
FIG. 42 shows a graph of quality factor versus position for a sample disposed in a resonator.
Figure 43:
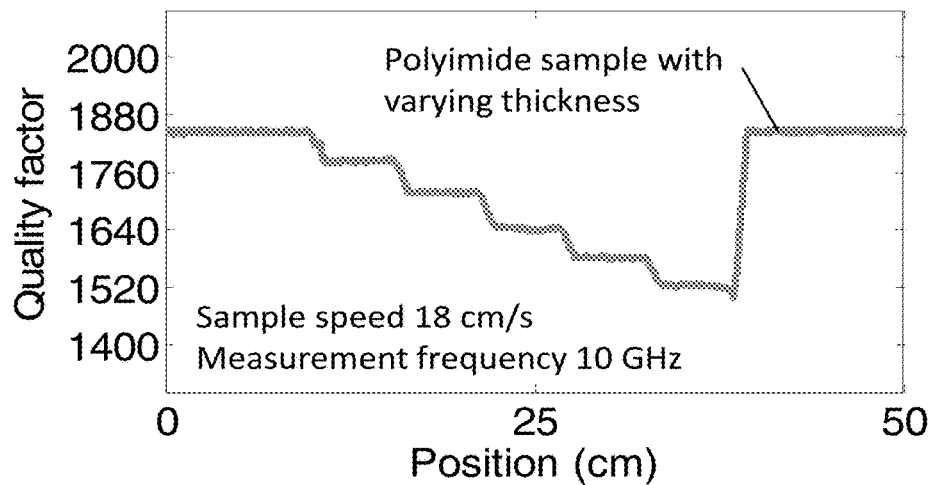
FIG. 43 shows a graph of quality factor versus position for a sample disposed in a resonator.

Example 3. Continuous Measurement of Resonance Frequency and Quality Factor of the Resonator From the best fit lines of resonance frequency and quality factor shown in FIG. 36 and FIG. 37, the best fit lines were used to map from first output signal 46 and second output signal (shown in FIG. 28 to FIG. 33) to the resonance frequency and quality factor, respectively. The result of this mapping is shown in FIG. 38, FIG. 39, FIG. 40 (for resonance frequency versus position of sample 60 disposed in resonator 52) and shown in FIG. 41, FIG. 42, and FIG. 43 (for quality factor versus position of sample 60 disposed in resonator 52). In certain applications, such as quality control, the resonance frequency and quality factor are used directly without further analysis of the data.

Figure 44:
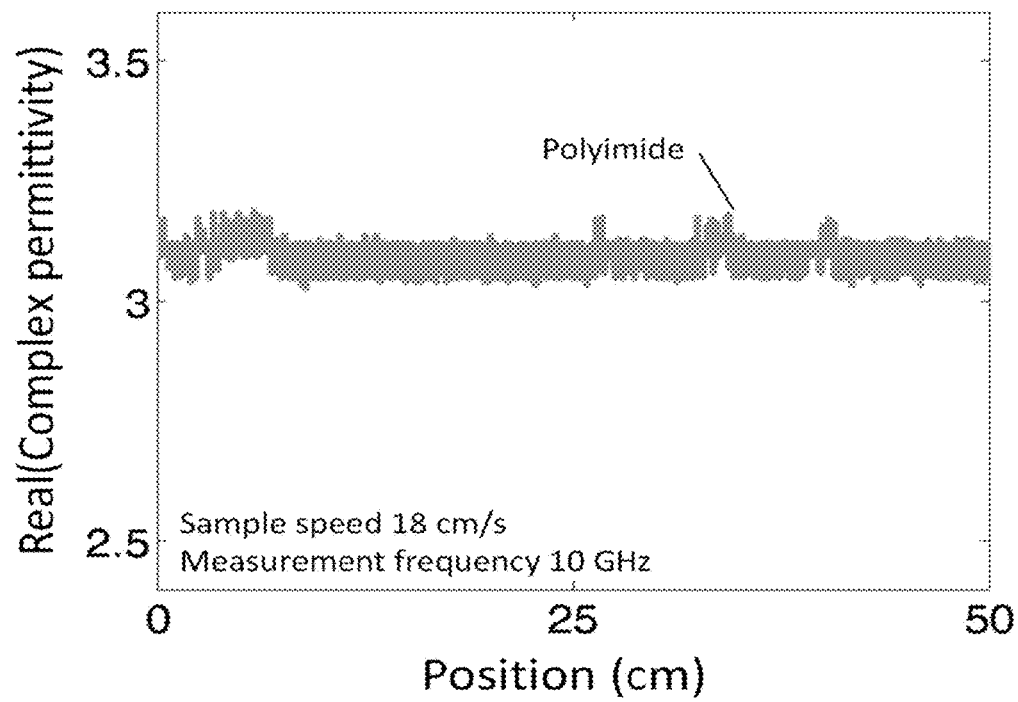
FIG. 44 shows a graph of a real part of complex permittivity versus position of a sample.

Example 4. Continuous Measurement of Complex Permittivity or Dielectric Constant and Conductivity Once the resonance frequency and quality factor of resonator 52 were recorded for polyimide sample 60 per Example 3, the real part of the complex permittivity was determined from formula (1). FIG. 44 shows a graph of the real part of the complex permittivity of polyimide sample 60 that was determined at an excitation signal frequency of 10 GHz for a length of 50 cm of sample 60 that was provided to resonator 52 at a feed rate of 18 cm/s through opening 78 in resonator 52. The real part of the complex permittivity was determined to be about 3.1, which was consistent with reported value of provided by the manufacturer of sample 60 at this frequency.

Figure 45:
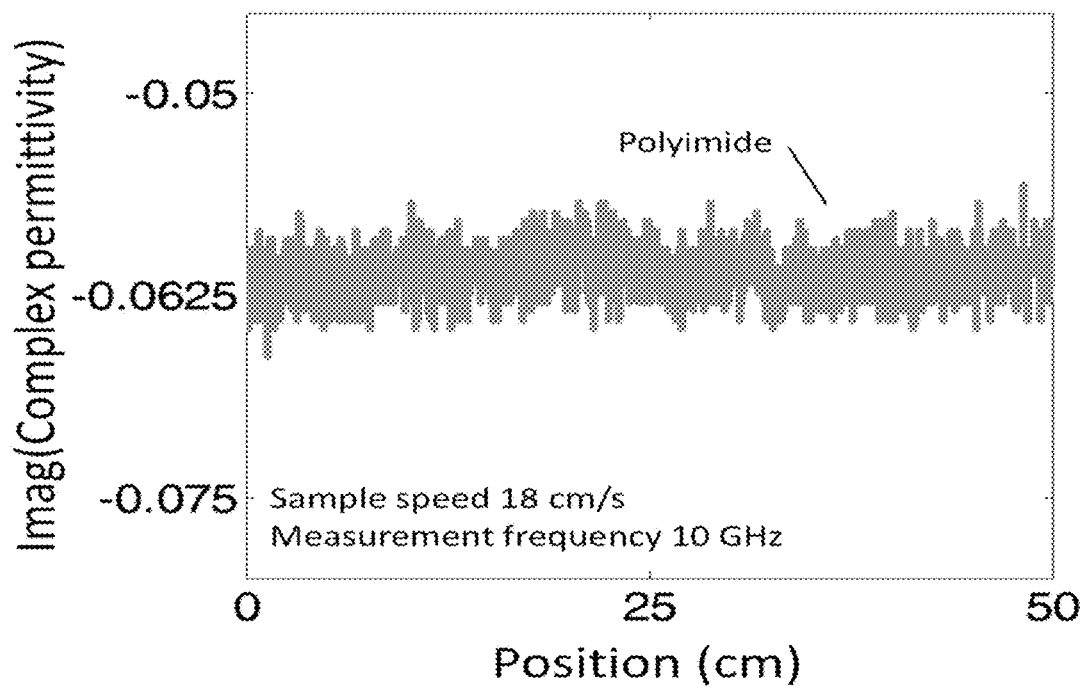
FIG. 45 shows a graph of an imaginary part of complex permittivity versus position of a sample.

FIG. 45 shows a graph of the imaginary part of the complex permittivity versus position of polyimide sample 60 determined at 10 GHz for a 50 cm length of sample 60 that moved at a feed rate of 18 cm/s through resonator 52.

Figure 46:
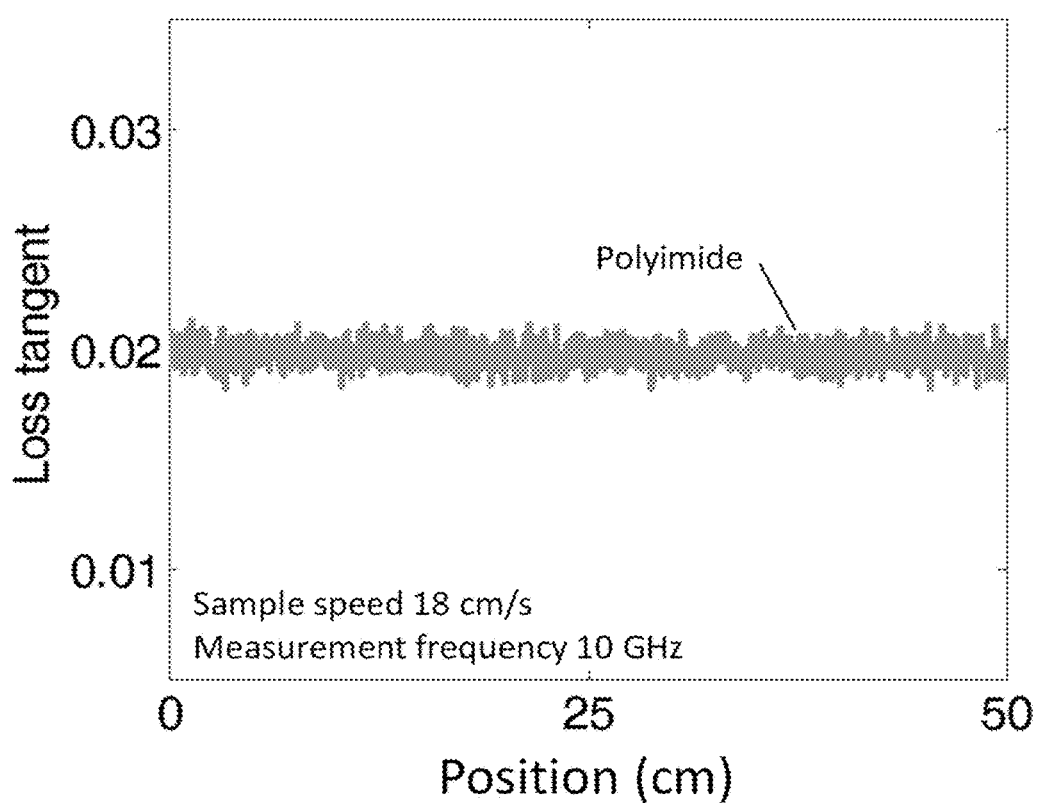
FIG. 46 shows a graph of loss tangent versus position of a sample.

In some embodiments, both real and imaginary parts of the complex permittivity are extracted to obtain the loss tangent. FIG. 46 shows a graph of the loss tangent versus a position of polyimide sample 60. The loss tangent was determined as a ratio of the imaginary part of the complex permittivity to the real part of the complex permittivity.

Example 5. Sample Thickness Measurement

The sample volume or a particular geometrical factor can be extracted for quality assurance and control applications. Formula (1) and formula (4) are inverted to solve for the effective sample volume for sample 60 with known real or imaginary complex permittivity. The volume of sample 60 solved from the resonance frequency of resonator 52 is provided by formula (7), and the volume of sample 60 determined from the quality factor of resonator 52 is provided by formula (8).

$$V_s \approx \left(\frac{V_c}{2\cdot(\epsilon_r - 1)}\right)\cdot\left(\frac{\omega_c - \omega_{cs}}{\omega_c} - b_r\right) \qquad (7)$$

$$V_s \approx \left(\frac{V_c}{4\epsilon_i}\right)\cdot\left(\frac{1}{Q_{cs}} - \frac{1}{Q_c} - b_i\right) \qquad (8)$$

Figure 47:
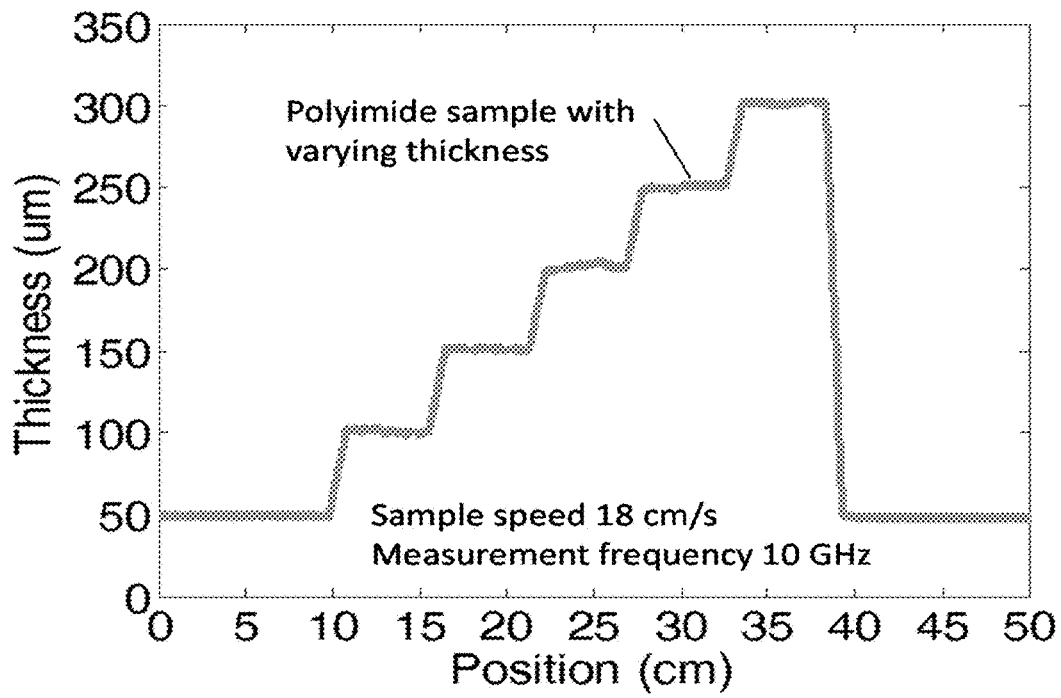
FIG. 47 shows a graph of sickness versus position of a sample.

After formula (7) and formula (8) were numerically evaluated, formula (2) was solved for the sample geometry. The thickness of polyimide sample 60 with varying thickness was determined at 10 GHz using formula (7), and FIG. 47 shows a graph of thickness versus position of sample 60.

Example 6. Sheet Resistance Measurement

A sheet resistance or conductivity of sample 60 can be extracted for a quality assurance or control application. Here, the imaginary part of the complex permittivity relates to the effective sample conductivity as provided by formula (9), $$\sigma \approx \epsilon_i\epsilon_o\omega_{cs} \qquad (9)$$

wherein the permittivity of the free space, $\epsilon_o$, is approximately $8.85\cdot10^{-12}$ Farads/meter. For sample 60 of known thickness t, the sheet resistance R relates to sample conductivity as provided by formula (10).

$$R \approx t/\sigma \qquad (10)$$

Figure 48:
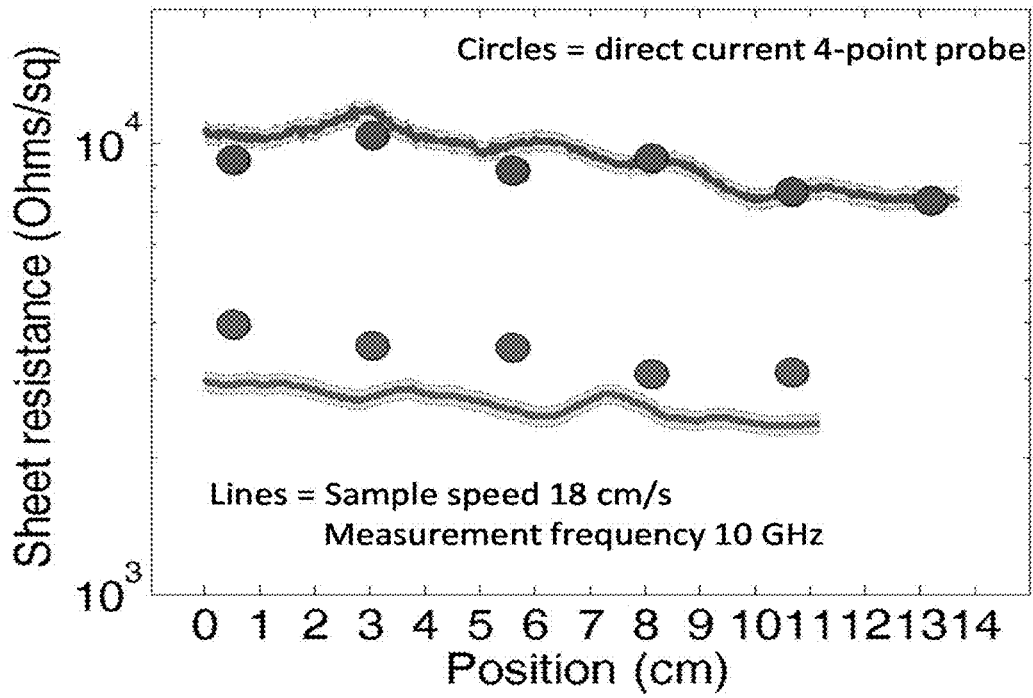
FIG. 48 shows a graph of sheet resistance versus position of a sample.

Two conducting thin films were used as samples. Electrical properties of the films were measured using a direct current four-point probe. The direct current four-point probe required that the sample was measured at different positions along the film. Once the sample was measured with the direct current four-point probe, the conducting thin films were measured by the noncontact resonameter of Example 1. FIG. 48 shows a graph of sheet resistance versus position of sample 60 with respect to resonator 52. Here, the noncontact resonameter provided sheet resistance values that were within twice the uncertainty of the direct current four-point probe measurement.

Example 7. Isolating the Contribution of an Unknown Layer in a Multilayered Sample Properties of samples that contain a plurality of layers can be determined with the noncontact resonameter of Example 1. Such samples can include, e.g., of a stack of layers, concentric circular layers, or a weave of fibers. The effect of the known layers to measurement with the noncontact resonameter can be subtracted from the total measured voltages (e.g., of first output signal 46 or second output signal 48) or the resonance frequency and quality factor of resonator 52. In an embodiment, the effect of the known layers contributes to the resonance frequency and quality factor as a parallel admittance. The total measured resonance frequency is provided by formula (11), and the quality factor is provided by formula (12).

$$\omega_{total}^{-2} = \omega_{unknown}^{-2} + \omega_{known}^{-2} + \omega_c^{-2} \tag{11}$$

$$Q_{total}^{-1} = Q_{unknown}^{-1} + Q_{known}^{-1} + Q_c^{-1} \tag{12}$$

Formula (11) and formula (12) can be used to obtain the left hand side of formula (1) and formula (4), respectively.

Example 8. Magnetic Properties Measurement

In some embodiments, magnetic properties of sample 60 are determined. Formula (1) and formula (4) are modified accordingly to extract the complex permeability. Accordingly, the change in the resonance frequency and quality factor of resonator 52 are due to the magnetic properties of sample 60 and the sample volume.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A noncontact resonameter comprising:
   a resonator to:
      produce an excitation signal comprising a field;
      subject a sample to the excitation signal;
      produce a first resonator signal in a presence of the sample and the excitation signal, the first resonator signal comprising:
         a first quality factor of the resonator;
         a first resonance frequency of the resonator; or
         a combination comprising at least one of the foregoing,
      the first resonator signal occurring in an absence of contact between the sample and the resonator; and
      produce a second resonator signal in a presence of the excitation signal and an absence of the sample, the second resonator signal comprising:
         a second quality factor of the resonator;
         a second resonance frequency of the resonator; or
         a combination comprising at least one of the foregoing;
   a circuit in electrical communication with the resonator to receive the first resonator signal and the second resonator signal, the circuit comprising:
      a diode that:
         receives the first resonator signal and the second resonator signal from the resonator; and
         produces a detector signal in response to receipt of the first resonator signal or the second resonator signal;
      a tunable resistor in electrical communication with the diode and that:
         receives the detector signal from the diode;
         controls a signal-to-noise ratio of the circuit; and
         tunes a measurement speed of the circuit;
      a first phase sensitive detector in electrical communication with the diode and that:
         receives the detector signal from the diode;
         receives a frequency output from a frequency source;
         samples at a first harmonic of the frequency output from the frequency source;
         produces in-phase signal in response to receipt of the detector signal and the frequency output;
      a process controller in electrical communication with the first phase sensitive detector and that:
         receives the in-phase signal from the first phase sensitive detector; and
         produces a first output signal in response to receipt of the in-phase signal;
      a bias tee in electrical communication with the frequency source and the process controller and that:
         receives the frequency output from the frequency source;
         receives the first output signal from the process controller; and
         produces a control signal in response to receipt of the frequency output and the first output signal;

a second phase sensitive detector in electrical communication with the diode and that:
receives the detector signal from the diode;
receives the frequency output from the frequency source;
samples at a second harmonic of the frequency output from frequency source; and
produces a magnitude signal in response to receipt of the detector signal and the frequency output;
the frequency source in electrical communication with the first phase sensitive detector and the second phase sensitive detector and that:
produces the frequency output;
controls a modulation frequency of a source signal produced by a source oscillator;
a second process controller in electrical communication with the second phase sensitive detector and that:
receives the magnitude signal from the second phase sensitive detector; and
produces a second output signal in response to receipt of the magnitude signal, the second output signal being communicated to the frequency source to control an amplitude of the frequency modulation of the source oscillator by changing an amplitude of the frequency source;
a continuous feeder to:
provide the sample proximate to the resonator;
dispose the sample intermediately in the field of the excitation signal during production of the first resonator signal;
remove the sample from the resonator;
manipulate a position of the sample relative to the resonator in a continuous motion and in an absence of contact between the sample and the resonator; and
a source in electrical communication with the resonator and that comprises:
the source oscillator that:
receives the control signal from the bias tee;
tunes selectively a center frequency of the source signal;
produces the source signal in response to receipt of the control signal; and
provides the source signal to the resonator, such that:
the resonator receives the and produces the excitation signal in response to receipt of the,
wherein the circuit is in electrical communication with the and produces a control signal in response to receipt of the first resonator signal, and
the comprises a phase and an amplitude that are based on the control signal, such that the circuit provides feedback to the source to detect a change in resonance frequency or quality factor of the resonator.

2. The noncontact resonameter of claim 1, wherein
a first harmonic of output power from the resonator signal produced by the resonator locks a center frequency of the excitation signal to a resonance frequency of resonator by changing an amplitude of the first output signal; and
a second harmonic of output power from the resonator signal produced by the resonator adjusts a depth of the frequency modulation of the source signal by tuning the second output signal.

3. The noncontact resonameter of claim 1,
wherein a power difference between a maximum and a minimum output power during a modulation cycle is constant, and
the second output signal is monotonically related to a quality factor of the resonator.

4. The noncontact resonameter of claim 1, wherein the resonator comprises a free-space resonator or a cavity resonator.

5. The noncontact resonameter of claim 4, wherein the resonator is the cavity resonator, and the cavity resonator comprises:
a wall bounding a sample space to receive the sample; and
an opening to transmit the sample to the sample space.

6. The noncontact resonameter of claim 4, wherein the resonator is the free-space resonator, and the free-space resonator comprises a sample space to receive the sample.

7. The noncontact resonameter of claim 1, wherein the continuous feeder traverses the resonator.

8. The noncontact resonameter of claim 1, wherein the circuit comprises a plurality of phase sensitive detectors to receive the first resonator signal and the second resonator signal.

9. The noncontact resonameter of claim 1, wherein the field of the excitation signal comprises an electromagnetic field or an acoustic field.

10. The noncontact resonameter of claim 1, wherein the first resonance frequency changes with a change in the dielectric constant of the sample subjected to the excitation signal, and the first quality factor changes with a change in the electrical conductivity of the sample subjected to the excitation signal.

11. The noncontact resonameter of claim 1, wherein the continuous feeder provides continuously a first portion of the sample to the resonator and removes continuously a second portion of the sample from the resonator.

12. The noncontact resonameter of claim 1, wherein the continuous motion is interruptible.

13. The noncontact resonameter of claim 1, wherein the continuous motion occurs substantially in a single dimension of travel of the sample relative to the resonator, from provision of the sample to the resonator to removal of the sample from the resonator.

14. The noncontact resonameter of claim 1, wherein the noncontact resonameter provides a measurement of a property of the sample, the property comprising an electrical property, a mechanical property, a geometric property, or a combination comprising at least one of the foregoing properties,
the property determined from the first resonator signal.

15. The noncontact resonameter of claim 14, wherein the property is the electrical property, and
the electrical property comprises a permittivity, a dielectric constant, an electrical conductivity, a permeability, or a combination comprising at least one of the foregoing electrical properties.

16. The noncontact resonameter of claim 1, wherein the circuit detects the first quality factor and the first resonance frequency simultaneously in real time in the presence of the sample, and
the circuit detects the second quality factor and the second resonance frequency simultaneously in real time in the absence of the sample.

* * * * *